United States Patent
Elia

(10) Patent No.: US 9,566,135 B2
(45) Date of Patent: Feb. 14, 2017

(54) METHOD OF GROWING AN ARTERY

(75) Inventor: James P. Elia, Scottsdale, AZ (US)

(73) Assignees: DENTAL MARKETING SPECIALISTS, INC., an Arizona Corp, Scottsdale, AZ (US), part interest; JERRY W. BAINS AND SALEE C. BAINS IRREVOCABLE TRUST, Carefree, AZ (US), part interest ( * ) Notice: Subject to any disclaimer, the term of this patent is extended or adjusted under 35 U.S.C. 154(b) by 991 days.

(21) Appl. No.: 11/986,690

(22) Filed: Nov. 26, 2007

(65) Prior Publication Data

US 2008/0095709 A1 Apr. 24, 2008

Related U.S. Application Data

(63) Continuation of application No. 09/064,000, filed on Apr. 21, 1998, now abandoned.

(51) Int. Cl.

| | |
|---|---|
| A61C 8/00 | (2006.01) |
| A61C 8/02 | (2006.01) |
| A61K 35/32 | (2015.01) |
| A61K 35/44 | (2015.01) |
| A61K 48/00 | (2006.01) |
| C12N 5/077 | (2010.01) |
| C12N 5/071 | (2010.01) |

(52) U.S. Cl.
CPC .............. *A61C 8/00* (2013.01); *A61C 8/0001* (2013.01); *A61C 8/0006* (2013.01); *A61C 8/0018* (2013.01); *A61C 8/0039* (2013.01); *A61K 35/32* (2013.01); *A61K 35/44* (2013.01); *A61K 48/005* (2013.01); *A61K 48/0058* (2013.01); *A61K 48/0075* (2013.01); *C12N 5/069* (2013.01); *C12N 5/0654* (2013.01); *C12N 2501/155* (2013.01); *C12N 2501/48* (2013.01); *C12N 2501/60* (2013.01)

(58) Field of Classification Search
None
See application file for complete search history.

(56) References Cited

U.S. PATENT DOCUMENTS 5,652,225 A * 7/1997 Isner ........................... 514/44 R
5,843,780 A * 12/1998 Thomson ...................... 435/363
7,097,832 B1 * 8/2006 Kornowski et al. ......... 424/93.7

OTHER PUBLICATIONS

Rabelink et al., Arteriosclerosis, Thrombosis, and Vascular Biology, 24:834-838, (2004).*
Strauer (2002, Circulation 106:1913-1918).*
"Paired box" http://www.ihop-net.org/UniPub/iHOP/?search=paired+box&field=all&ncbi__tax__id=9606&organism__syn=accessed Mar. 9, 2009.*
Janssen et al., (Journal of Hematotherapy, 1:349-359 (1992)).*
Dohmann et al., 2005 Circulation. Jul. 26, 2005;112(4):521-526.*
Roufosse et al., (Int J Biochem Cell Biol. Apr. 2004;36(4):585-597.*
Trigg (Pediatric Transplantation, Dec. 2002;6(6):465-474).*
The Journal of Invasive Cardiology, (vol. 17, Jul. 1, 2005, Issue No. 7) "Tissue Engineering and Interventional Cardiology" (No author) (http://www.invasivecardiology.com/article/4347).*
Definition of "autocrine" in the Free Dictionary http://medical-dictionary.thefreedictionary.com/autocrine.*
Isner et al., Circulation 91:2687, (Jun. 1, 1995).*
Ziegelhoeffer et al., Circulation Res. 94:230 (2004).*
Strauer & Kornowski, Circulation 107:929 (2003).*
Augustin, Circulation Res. 89:645 (2001).*
Incredulous legal definition: http://legal-dictionary.thefreedictionary.com/incredulous; accessed Apr. 10, 2013.*
Incredulous, Webster's dictionary: http://machaut.uchicago.edu/?resource=Webster%27s&word=incredulous&use1913=on ;accessed Apr. 10, 2013.*
Noishiki et al., Nat. Med. Jan. 1996;2(1):90-93.*
International Search Report, dated Nov. 30, 2007, issued in International Application Serial No. PCT/US03/19147 (includes four (4) references).
University of South Florida website: www.research.usf.edu 2003 Publication. CMDC #088. Effective Jan. 2003, entitled, "Mouse Cytokines: Sources. Cellular Targets, and In Vivo Effects".

* cited by examiner

*Primary Examiner* — Joanne Hama
(74) *Attorney, Agent, or Firm* — Gerald K. White; Charles N. Lovell

(57) ABSTRACT

An organ derived from genetic material is inserted in a patient's body. Genetic material is inserted at a selected site in the body to grow an organ.

1 Claim, 10 Drawing Sheets

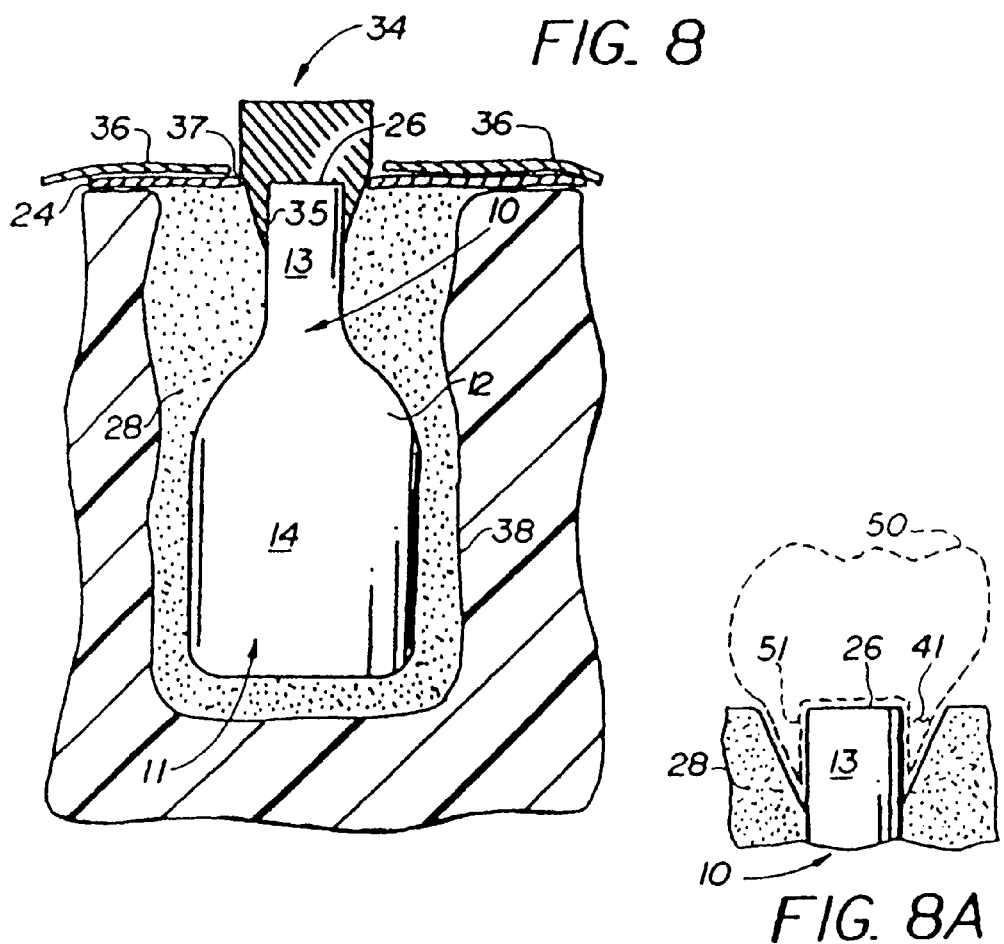
FIG. 8
FIG. 8A
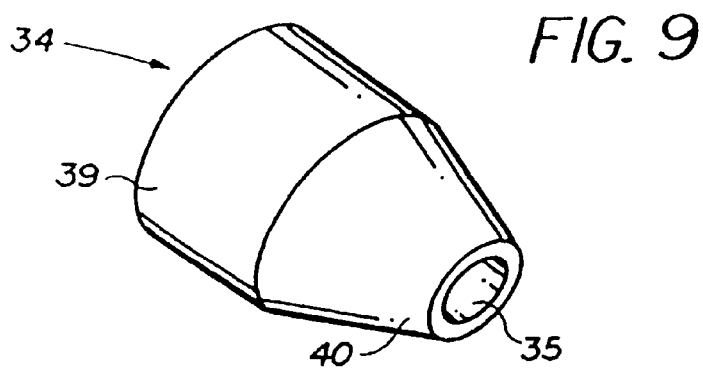
FIG. 9

METHOD OF GROWING AN ARTERY

This application is a continuation of application Ser. No. 09/064,000, filed Apr. 21, 1998 now abandoned.

This invention relates to a method and apparatus for installing a dental implant in the alveolar or basal bone of a patient.

More particularly, the invention relates to a method and apparatus for a dental implant which reduces the likelihood of the implant becoming infected, which does not require an opening of precise size to be drilled or formed in the alveolar bone to receive the dental implant, which can mount an implant on existing alveolar bone without requiring alteration of the structure of the bone, which prevents the juncture of the dental implant and artificial tooth attached to the implant from being exposed in the event the patient's gums recede, which enables bone mass lost as the patient ages to be replaced, and which enables an implant to be used when drilling an opening in the alveolar bone is precluded due to the existence of a nerve in the bone.

Dental implants are well known in the art. See, for example, U.S. Pat. No. 5,006,070 to Komatsu, U.S. Pat. No. 4,693,686 to Sendax, U.S. Pat. No. 4,812,120 to Flanagan et al., U.S. Pat. No. 4,818,559 to Hama et al., U.S. Pat. No. 4,671,768 to Ton, and U.S. Pat. No. 4,175,565 to Chiarenza et al. Such prior art dental implants and methods for installing the same have disadvantages.

First, the implants normally must be press fit or wedged into an opening formed in the alveolar bone. Force fitting an implant into the alveolar bone is not desirable because it is uncomfortable for the patient, runs the risk of cracking the jaw bone, further damages the bone, and, most importantly, increases the likelihood of infection because dental implants ordinarily are provided with an assortment of ridges, points, or teeth which serve as desirable sites for bacteria, both before and after the implant is inserted in the bone. As a consequence, dental implants typically appear medieval.

Second, force fitting an implant in the alveolar bone requires that the opening formed in the bone have a specific size which roughly conforms to the outer dimensions of the implant so the implant can be force fit into the opening. If a dental surgeon selects a drill of improper size, or waggles the drill while forming the hole in the alveolar bone, the implant may not seat properly in the bone and will work free from the jaw.

Third, the surface area of the portion of the implant imbedded in the jaw is typically reduced because of the common belief that fenestrations of various size must be formed in the implant to permit bone to grow through and anchor the implant.

Fourth, conventional implant procedures often can not be used because the drilling of a opening in the alveolar bone is prohibited by a nerve which passes through the bone.

Fifth, conventional implant procedures also often can not be successfully used when the jaw bone has significantly receded, as can be the case with older patients.

Sixth, conventional implant procedures do not offer a way of replacing alveolar bone which has been lost due to aging or to some other cause resulting in injury to the bone.

Seventh, conventional implant procedures typically do not permit the ready adjustment of the position of the implant after the implant is inserted in the opening formed in the alveolar bone. Correcting the position of an improperly installed implant is often difficult, unless the implant is completely removed from the alveolar bone, which is a time consuming process.

Accordingly, it would be highly desirable to provide an improved dental implant method and apparatus which would not require the force fitting of an implant in the alveolar bone, would not require the formation of a specific size opening in the jaw bone, would provide an implant less likely to loosen after being inserted in the alveolar bone, would permit an implant to be used on alveolar bone housing a nerve, would enable implants to be successfully utilized on alveolar bone which has receded with age, and would permit the position of the implant to be readily adjusted after the implant is inserted in an opening in the alveolar bone.

Therefore, it is a principal object of the invention to provide an improved dental implant method and apparatus.

Another object of the invention is to provide an improved dental implant which can be inserted in an opening in the alveolar bone without requiring that the opening must, within close tolerances, have a specific shape and dimension.

A further object of the invention is to provide an improved dental implant which permits ready adjustment of the position of the implant after the implant is placed in an opening formed in the jawbone.

Still another object of the invention is to provide a dental implant method which permits an implant to be attached to alveolar bone housing a nerve.

Yet a further object of the invention is to provide a dental implant method which allows an implant to be utilized on alveolar bone which has experienced significant loss and recession of its mass.

Another and further object of the instant invention is to provide an improved dental implant which is less likely to loosen after insertion in the alveolar bone.

These and other, further and more specific objects and advantages of the invention will be apparent to those skilled in the art from the following detailed description thereof, taken in conjunction with the drawings, in which:

FIG. 8 is a side partial section view illustrating an alternate embodiment of the implant of the invention inserted in an opening formed in the alveolar bone;

FIG. 8A is a side view illustrating a portion of the implant of FIG. 8 after the healing cap is removed;

FIG. 9 is a perspective view illustrating a healing cap used in the implant of FIG. 8;

Figure 1:
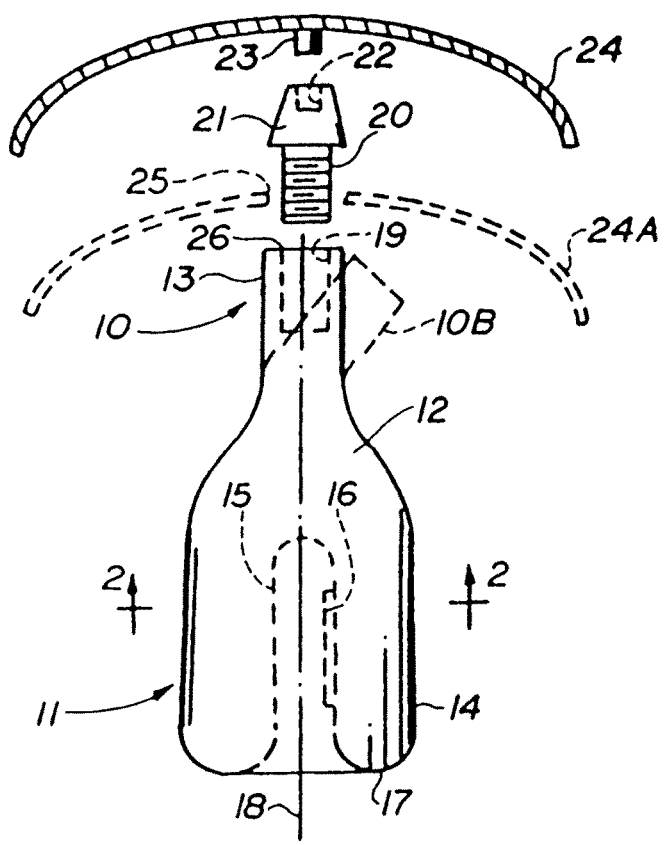
FIG. 1 is a front view of a dental implant apparatus constructed in accordance with the principles of the invention.

Briefly, in accordance with my invention, I provide an improved dental implant. The implant comprises a body having a closed top and a bottom and a longitudinal axis extending through the top and bottom; and, a head supported on the top of the body and adapted to support an artificial tooth. The body extends downwardly from the top and terminates at a lower end remote from the head. The body includes a smooth continuous surface extending from the top to the bottom and defining the periphery of the top and the bottom. The smooth surface circumscribes the longitudinal axis. The body also includes a hollow centrally defined therein, circumscribed by the continuous surface, and extending into the body through the bottom a selected distance toward the top. The hollow only opens at the lower end of the body. The head can have a smaller width than the body. The hollow can be an involute. The continuous surface can be shaped such that when any cross section of the body is taken perpendicular to the longitudinal axis, each point on the continuous surface is generally equidistant from the longitudinal axis.

In another embodiment of the invention, I provide a method of anchoring a dental implant in the alveolar bone of a patient. The method comprises the steps of forming an opening in the alveolar bone; inserting a dental implant in the opening, the implant comprising a body and a head supported on the body and adapted to support an artificial tooth, the dental implant only partially filling the space in the opening; and, packing the space in the opening which is unoccupied by the dental implant with a hydroxyapatite composition. The opening can be large enough to permit the implant to be readily tilted from side to side after insertion in the opening. After the opening is packed with hydroxyapatite composition, the implant can be adjusted or tilted from side to side and the hydroxyapatite composition then repacked.

In a further embodiment of the invention, I provide a dental implant comprising a body; a head supported on the body and having a longitudinal axis and including an upper portion adapted to support an artificial tooth and having a distal tip and a peripheral surface circumscribing the longitudinal axis and extending downwardly from the distal tip toward the body, and, a lower portion supported on the body; and, a healing cap. The healing cap is adapted to be removably attached to the upper portion of the head and includes a prophylactic portion which, when the healing cap is attached to the upper portion, slidably extends downwardly from the tip over and covers at least a portion of the peripheral surface such that when the implant is inserted in an opening in the alveolar bone, a solidified filler composition at least partially fills the opening, extends downwardly from the distal tip toward the body, and covers the prophylactic portion, the lower portion, and the body, and the healing cap is removed from the head, a space exists intermediate the portion of the peripheral surface and the solidified filler composition such that an artificial tooth can extend into the space and cover the distal tip of the head. The filler composition can be a hydroxyapatite composition.

In still another embodiment of the invention, I provide a method of anchoring a dental implant to the alveolar bone of a patient. The method comprises the steps of placing the dental implant at a selected site on the alveolar bone, the dental implant comprising a body and a head supported on the body and adapted to support an artificial tooth; packing a malleable hydroxyapatite composition around the dental implant and against alveolar bone of the patient; and, covering the malleable hydroxyapatite composition with a pliable sheet of material to at least partially prevent gum tissue from growing into the hydroxyapatite composition while the hydroxyapatite composition solidifies.

In yet another embodiment of the invention, I provide a dental implant for a ridge of alveolar bone normally at least partially covered by gum tissue. The implant comprises a body having a top and a pair of opposed feet each extending downwardly from the top to a tip at a lower end remote from the top, the feet having an inner surface shaped, contoured, and dimensioned to conform to the ridge of alveolar bone when the gum tissue is removed from the ridge; and, a head supported on the body and adapted to support an artificial tooth.

In yet still another embodiment of the invention, I provide a method of anchoring a dental implant to the existing alveolar bone of a patient, the bone having an existing outer surface. The method comprises the steps of removing alveolar bone to form an outwardly projecting anchor peg having a selected shape and dimension; and, inserting a dental implant over the anchor peg. The dental implant comprises a body and a head support on the body and adapted to support an artificial tooth. The body extends downwardly from the head to a lower end remote from the head and having an aperture formed in the lower end. The aperture is shaped and dimensioned to be slidably inserted on and conform to the outwardly projecting anchor.

Turning now to the drawings, which depict the presently preferred embodiments of the invention for the purpose of illustrating the practice thereof and not by way of limitation of the scope of the invention and in which like reference characters refer to corresponding elements throughout the several views, FIG. 1, illustrates dental implant apparatus which is constructed in accordance with the principles of the invention and includes a dental implant which has the general shape of a wine bottle and includes a cylindrical head 10 attached to a body 11. The closed top 12 of body 11 has a smooth continuous conical outer surface which tapers from the smooth continuous outer cylindrical surface 14 of the bottom 11 into the smooth cylindrical outer surface 13 of head 10. The conical outer surface of top 12, as do smooth cylindrical surfaces 14 and 13, completely circumscribes longitudinal axis and centerline 18. Head 10 can, if desired, be bent at some selected angle with respect to axis 18 and body 11 as indicated by dashed lines 10B or can be tapered in the manner of head 10A in FIG. 12. The bottom of body 11 extends downwardly from the top 12 and terminates at lower end 17 remote from the head 10. Involute or hollow 15 is formed centrally within body 11, is circumscribed by continuous surface 14, and extends upwardly into body 11 a selected distance toward top 12. Hollow 15 opens only at the lower end 17. Head 13 has a smaller diameter than body 11. An internally threaded aperture 19 is formed in head 13 to receive the externally threaded end 20 of a healing cap. The frustroconical head 21 of the healing cap has a cylindrical aperture 22 formed therein. Cylindrical member 23 is attached to pliable fabric sheet 24 and is shaped to be removably snap fit into aperture 22. The sheet 24 can be secured to the healing cap or head 10 using any convenient means. For example, an aperture 25 can be formed through a pliable sheet 24A and sized such that end 20 slides through aperture 25 and permits sheet 24A to be compressed between head 21 and the circular distal end 26 of head 10. Rib 16 outwardly depends from the smooth cylindrical wall circumscribing and defining hollow 15 and, when hollow 15 is filled with hydroxyapatite or bone in a manner which will be described, prevents the dental implant from rotating about axis 18. Most infection in a tooth begins at the gum line and works its way downwardly toward the root of the tooth. The smooth continuous outer surfaces 13, 14 of the implant of FIG. 1 facilitate determining how far, if at all, infection has penetrated downwardly along the outer surfaces of the implant. The extension of the outer surfaces of the implant from the distal end 26 of the head to the lower end 17 make it difficult for infection to enter hollow 15. In many conventional implants, once infection extends a short distance into the bone, it is a simple matter for the infection to spread laterally under portions of the implant. Consequently, in the implant of FIG. 1 it is important that perforations are not formed through the continuous outer surfaces 13, 14, or the conical surface of top 12. The large area of surfaces 13 and 14 and of the outer conical surface of top 12 help distribute the forces which are produced on an artificial tooth mounted on the implant and decrease the likelihood that the implant will come loose. The smooth curvature and lack of ridges or points extending outwardly from implant surfaces 13 and 14 also decreases the likelihood that stress fractures will be formed in the alveolar bone during the use of an artificial tooth attached to the implant.

Figure 2:
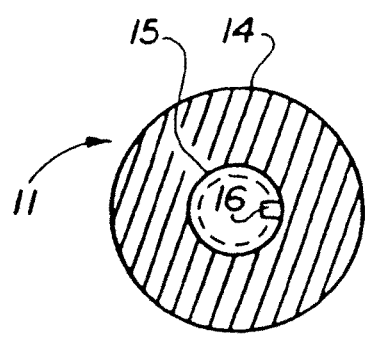
FIG. 2 is a section view of the dental implant apparatus of FIG. 1 illustrating internal construction details thereof.
Figure 3:
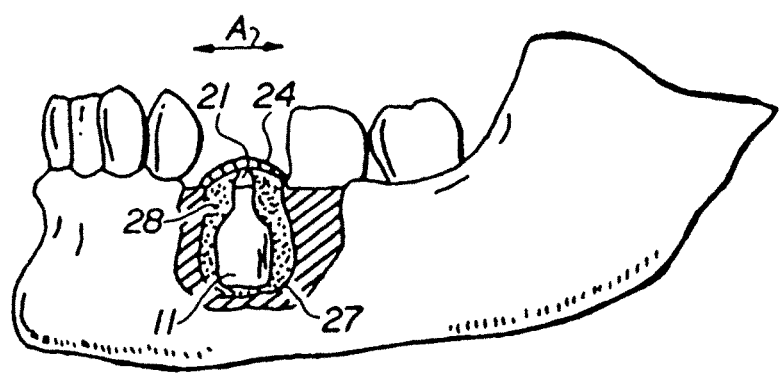
FIG. 3 is a side view of a portion of the lower jaw bone illustrating the implant of FIG. 1 installed in an opening formed in alveolar bone.
Figure 4:
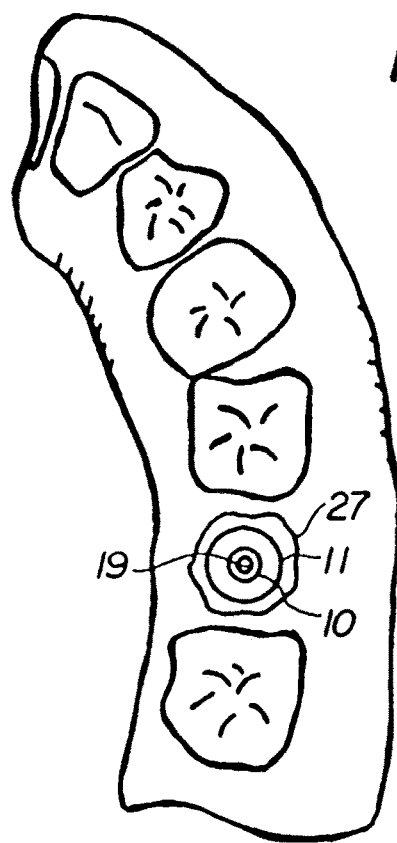
FIG. 4 is a top view of a portion of the jaw bone of FIG. 3 further illustrating the installation of the implant of FIG. 1 therein.
Figure 5:
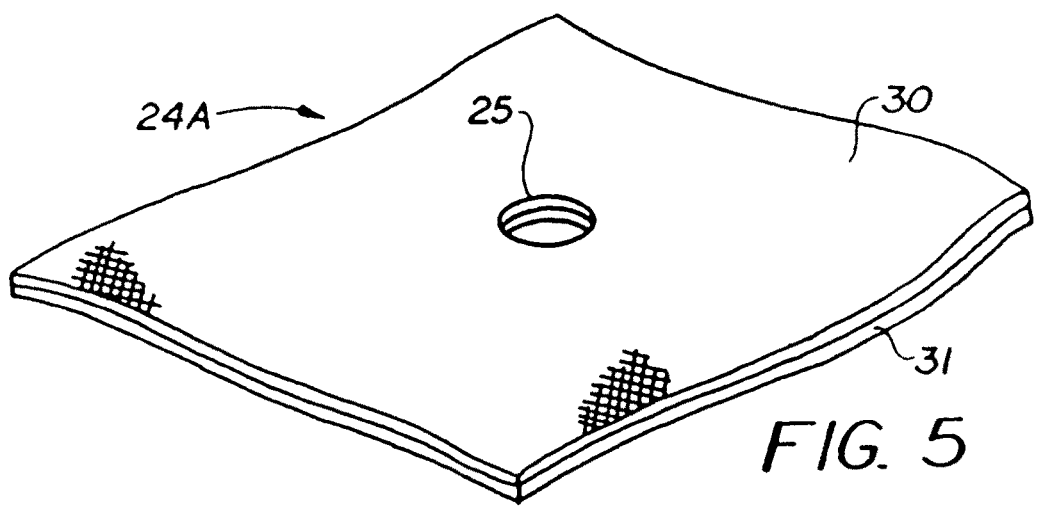
FIG. 5 is a perspective view illustrating a sheet of protective material used to shield hydroxyapatite composition used to pack an implant into an opening in the alveolar bone.

The installation of the implant apparatus of FIGS. 1 and 2 in alveolar bone is illustrated in FIGS. 3 and 4. As shown in FIG. 4, an opening 27 is drilled or otherwise formed at a selected location in the alveolar bone and the dental implant is inserted in opening 27. FIG. 4 illustrates opening 27 immediately after the dental implant has been inserted therein. Opening 27 is larger than the dental implant so that the head 10 can be grasped manually or with a dental instrument and tilted from side to side in opening 27. The space between the dental implant and the sides of opening 27 which circumscribe the implant is packed with a malleable hydroxyapatite composition 28. Hollow 15 can also be packed with the hydroxyapatite composition 28 before the implant is inserted in opening 27. After the composition 28 is packed into opening 27 around the dental implant, the head 10 can, if desired, be laterally moved in directions like those indicated by arrows A to tilt and reposition the implant in opening 27. After the dental implant is in the desired position in opening 27, the hydroxyapatite composition is repacked, and member 23 is snapped into aperture 22 in head 21 to position sheet 24 over opening 27 in the manner illustrated in FIG. 3. Sheet 24 can be trimmed as appropriate to cover opening 27. Although not shown in FIG. 4, gum tissue ordinarily at least partially covers and helps maintain sheet 24 in its desired position. Sheet 24 can comprise GORTEX or any other suitable pliable material which helps prevent, gum tissue from growing into the hydroxyapatite composition while it solidifies. If desired, sheet 24 can comprise a resorbable material. The GORTEX is left in place for a period of two to twelve months while the surrounding bone grows into and causes the hydroxyapatite composition to solidify and anchor the dental implant in place. After the hydroxyapatite composition has solidified, the healing cap and the sheet 24 are removed such that the gum tissue covers the solidified hydroxyapatite composition. The internally threaded aperture 19 in the head 10 of the implant is used to attach an artificial tooth to the implant.

GORTEX is produced by W. L Gore & Assoc., Inc. Regenerative Technologies of 3773 Kaspar Avenue, Flagstaff, Ariz. 86003-2500, USA. If desired, a pliable sheet 24A can include a layer of GORTEX or similar pliable material laminated with an undercoating of collagen, polyglycolic acid, or another desired material. The collagen imparts a stiffness to sheet 24A and over time is gradually dissolved by the body. GORTEX is an expanded polytetrafluoroethylene (e-PTFE) material.

Hydroxyapatite is a crystalline substance containing calcium and phosphorus and is found in certain rocks. It is the basic constituent of bone. The hydroxyapatite composition used to pack opening 27 can simply comprise a dry hydroxyapatite powder. The hydroxyapatite is, however, normally mixed with a liquid substance to form a slurry or more malleable composition which is more readily packed and remains in fixed position than dry hydroxyapatite powder. Hydroxyapatite powder can be mixed with water, plaster, collagen, dextran, epinephrine, or some other desirable material. The hydroxyapatite can be obtained from natural mineral sources, from ground bone, etc. Materials other than hydroxyapatite compositions can be used to fill and pack opening 27. Such other materials can include organic and inorganic matrices and/or combinations thereof. These matrices can be porous, non-porous, active and/or resorbable matrices, or totally inert. For example, coral and coral analogs, polymethyl methacrylate, polyethylene, PTFE (polytetrafluoroethylene), polysulfone, polymers, polyethylene glycols, osteomin (bone ash), autogenous bone, freeze dried demineralized bone, resorbable and non-resorbable hydroxyapatite, xenographs (bovine), miniscrews, allografts, composites, polyethylene glycol propionaldehyde, HAPSET, or the patient's own bone can be utilized.

Figure 6:
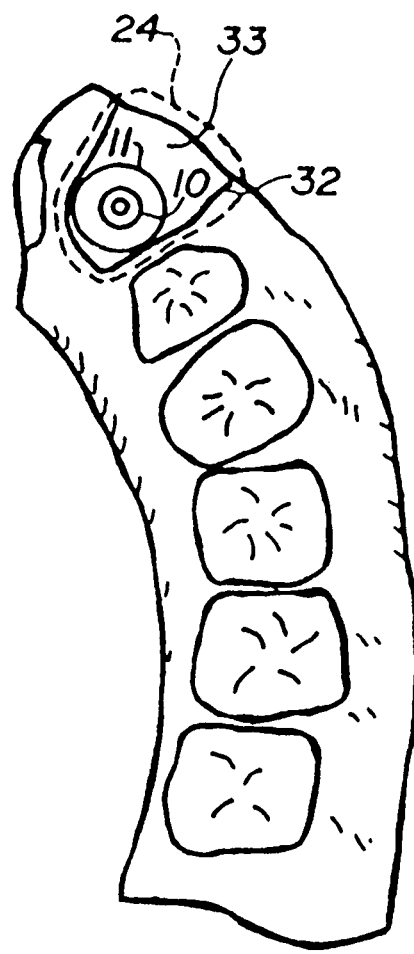
FIG. 6 is a top view of a portion of the lower jaw bone illustrating the insertion of an implant in an opening formed by laterally drilling into the jaw bone.
Figure 7:
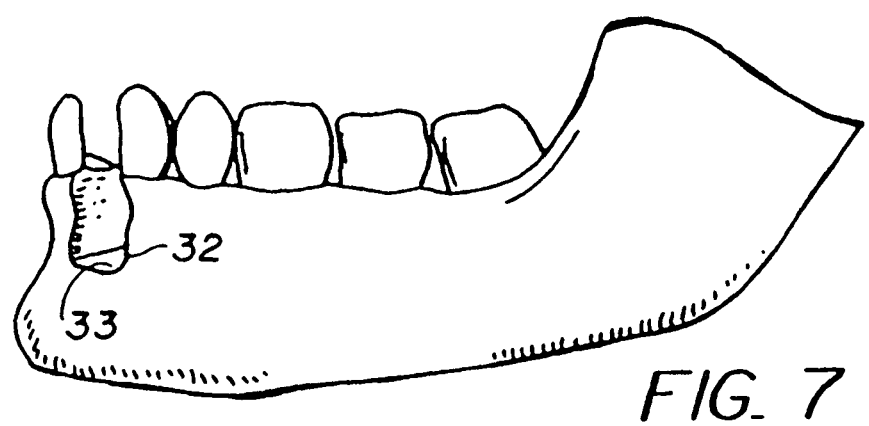
FIG. 7 is a side view of the jaw bone of FIG. 7 further illustrating the lateral opening formed in the jaw bone.

In some cases, it is preferable to produce an opening for a dental implant by forming an aperture in the alveolar bone which opens laterally or outwardly away from the inside of the patient's mouth. Such an outwardly opening aperture 32 is illustrated in FIGS. 6 and 7. In FIG. 7, the dental implant has not yet been inserted on floor 33 of aperture 32. FIG. 6 illustrates the implant in aperture 32. A malleable hydroxyapatite composition is utilized to pack the dental implant in aperture 32. Once aperture 32 is packed with hydroxyapatite composition and the implant is properly positioned in the hydroxyapatite composition and aperture 32, a healing cap is used to attach a pliable layer 24 of material to head 10 to protect the hydroxyapatite composition from invasion by epithelial or other living tissue while the composition hardens. After an appropriate period of time has passed and the bone has grown into and hardened the hydroxyapatite composition, the healing cap and layer of material are removed and an artificial tooth is attached to head 10 using internally threaded aperture 19.

An alternate embodiment of a healing cap 34 is illustrated in FIGS. 8 and 9. Cap 34 includes internal cylindrical aperture 35 shaped to slidably fit over the circular distal end 26 of head 10 and to cover at least a portion of the cylindrical peripheral surface 13 of head 10 of the wine bottle shaped implant of FIG. 1. The pliable sheet 24 in FIG. 8 has a circular aperture 37 formed therethrough which is large enough to slide a selected distance up the conical tip of cap 34, in the manner shown in FIG. 8, but which is too small to slide over the cylindrical upper end 39 of cap 34. Consequently, the conical end 40 of cap 34 functions to hold the sheet 24 in position against the hydroxyapatite composition 28 in the manner illustrated in FIG. 8. Further, a portion of the conical end 40 of cap 34 extends downwardly along surface 13 and past end 26 so that after the composition 28 has solidified and cap 34 is removed from head 10, a conically shaped space 41 (FIG. 8A) exists intermediate the solidified composition 28 and the upper portion of surface 13. When an artificial tooth 50 is subsequently attached to head 10 using the internally threaded aperture 19 formed therein, the lower portion of tooth 50 can include a cylindrical aperture 51 which slides over the upper end of head 10 and covers distal end 26. As would be appreciated by those of skill in the art, either sample implants or impression analogs of the head 10, 10A (FIG. 12) of the support member 70 (FIG. 12) of each implant can be provided to a dental laboratory so that the lower margins of an artificial tooth 50 can be perfectly sized to extend into and completely fill the conically shaped space 41. Distal end 26 ordinarily is positioned at the gum line after the implant is inserted in an opening 38 formed in the alveolar bone. Accordingly, the portions of the artificial tooth 50 extending into space 41 extend below the gum line of the patient.

Figure 10A:
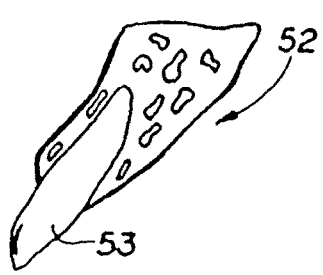
FIG. 10A is a side section view illustrating normal alveolar bone structure around an incisor tooth.
Figure 10B:
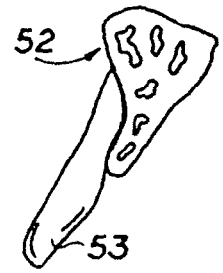
FIG. 10B is a side section view illustrating the recession of the alveolar bone structure from around the incisor tooth of FIG. 10A.
Figure 10C:
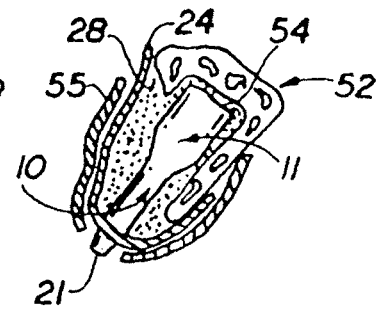
FIG. 10C is a side view illustrating the insertion of an implant in the bone structure of FIG. 10C after the incisor tooth is removed or falls out.

FIG. 10A illustrates a normal, healthy alveolar bone 52 supporting an incisor tooth 53. In FIG. 10B, the bone 52 has receded due to age or other factors. In FIG. 10C, tooth 53 has been removed; a cylindrical aperture 54 has been drilled or otherwise formed in the bone 52; an implant has been inserted in aperture 54; a malleable hydroxyapatite composition 28 has been packed into aperture 54, around the implant, and against the bone 52; a layer of pliable material 24 has been attached to head 10 with the head 21 of a healing cap and extends over the hydroxyapatite composition 28; and, the gum tissue has been positioned over material 24. After the bone 52 grows into the hydroxyapatite composition 28 and the composition 28 solidifies, the healing cap and material 24 are removed, and an artificial tooth is attached to head 10. The hydroxyapatite composition applied to the implant and bone 52 in FIG. 10C is used to augment or build the bone 52 back up to a shape and dimension resembling or duplicating its original normal shape and dimension illustrated in FIG. 10A. A particular advantage of the dental implant methodology of the invention is that it permits hydroxyapatite compositions to be used to augment and enlarge existing alveolar bone structure while at the same time facilitating the anchoring of an implant to alveolar bone. To facilitate the anchoring of an implant in the existing alveolar or basal bone, indents or grooves can be formed in the bone or in the surface of the implant to receive hydroxyapatite or other material used to fill or pack into or around the alveolar or basal bone and the implant.

Figure 10D:
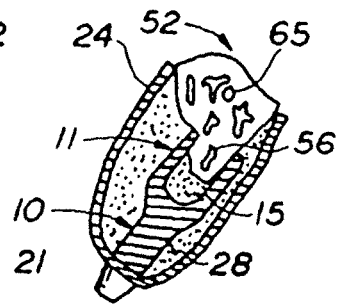
FIG. 10D is a side view illustrating the alveolar bone structure of FIG. 10B after the incisor tooth is removed and a circular drill is used to cut away some of the alveolar bone to form a cylindrical anchor peg.
Figure 10E:
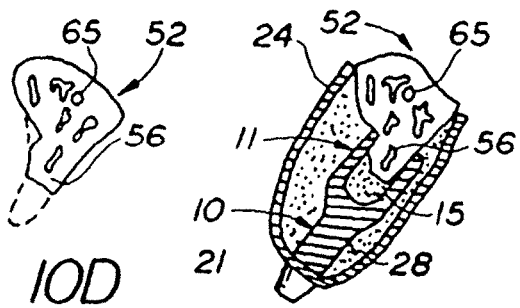
FIG. 10E is a side partial section view illustrating a dental implant slidably installed on the anchor peg of FIG. 10D and packed with a malleable hydroxyapatite composition.

In FIG. 10D, the tooth 53 has been removed from the alveolar bone 52 of FIG. 10B and a circular drill has been used to remove some of the bone 52 to form a cylindrical anchor peg 56 which is shaped and dimensioned to be slidably received by the involute 15 of the implant of FIG. 1 in the manner illustrated in FIG. 10E. After involute or hollow 15 is slid onto peg 56, malleable hydroxyapatite composition is packed around the body 11 and head 10 of the implant and the head 21 of the healing cap is used to attach pliable material 24 to head 10. If desired, hydroxyapatite composition 28 can also be inserted in hollow 15 before hollow 15 is slid onto peg 56. One the hydroxyapatite composition has solidified, the healing cap and material 21 are removed, and an artificial tooth is attached to head 10. The bone 52 illustrated in FIGS. 10D and 10E includes a nerve 65.

Figure 10F:
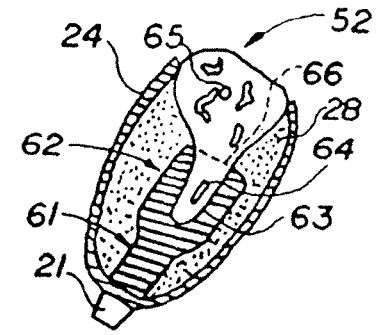
FIG. 10F is a side partial section view illustrating the alveolar bone structure of 10B after the incisor tooth is removed and an implant is slid onto the existing alveolar bone structure without altering the structure.
Figure 11:
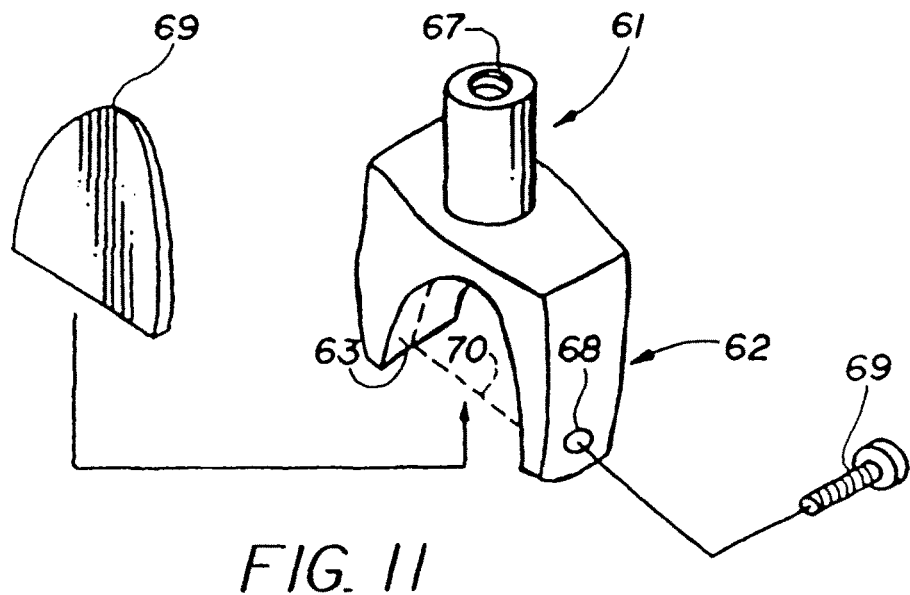
FIG. 11 is a perspective view illustrating an implant of the type which can be fit to an existing alveolar bone structure.

In FIG. 10F, the tooth 53 has been removed from the alveolar bone 52 of FIG. 10B and shape of the ridge 64 of bone 52 has not been altered. An implant has been placed on ridge 64. The implant includes head 61, body 62, and arch or U-shaped aperture 63. Aperture 63 is shaped and dimensioned to conform to and slide on to ridge 64 in the manner illustrated in FIG. 10F. The implant of FIG. 10F can be formed by making a mold of ridge 64 and using the mold to eventually produce an implant with an aperture 63 which will conform to ridge 64. Various techniques for making a mold of ridge 64 and using the mold to produce a duplicate of the ridge or to produce a shape which will conform to the ridge 64 are well known in the art and will not be discussed herein. After the implant of FIGS. 10F and 11 is slidably inserted on ridge 64 in the manner shown in FIG. 10F, malleable hydroxyapatite composition is pressed against and molded around against the implant and bone 52 and covered with a layer 24 which is secured to head 61 by head 21 of the healing cap illustrated in FIG. 1. The externally threaded end 20 of the healing cap is rotated into internally threaded aperture 67 formed in the upper end of head 61. If desired, an aperture(s) 68 can be formed through body 62 to permit a screw(s) to pass through the aperture 68 and into the bone 52 to secure the implant to the bone 52. In addition, a slot, indicated by dashed lines 66 in FIG. 10F, can be cut through ridge 64 to receive a panel 69 which is attached to arch 63 in the position indicated by dashed line 70.

Figure 12:
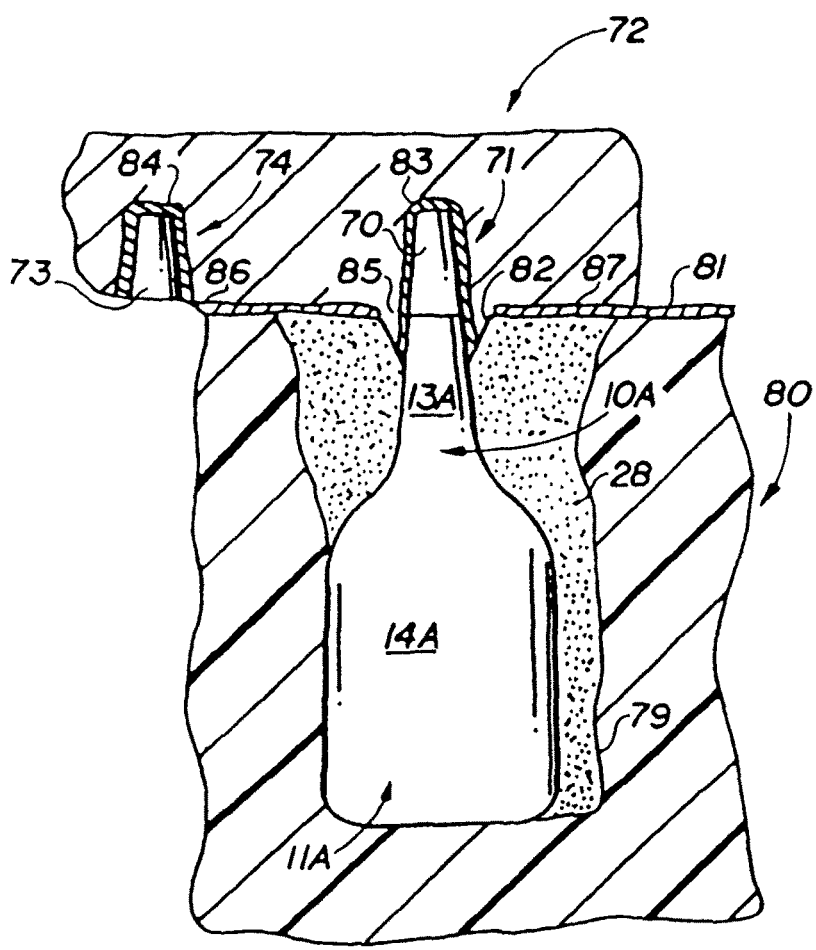
FIG. 12 is a side partial section view illustrating a molding procedure utilized in another embodiment of the invention.
Figure 13:
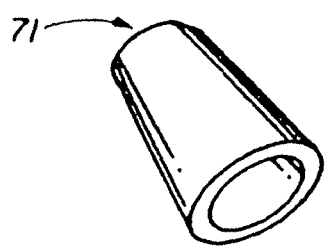
FIG. 13 is a perspective view of a sacrificial coping utilized in the embodiment of the invention illustrated in FIG. 12.

FIGS. 12 to 15 depict apparatus using in a molding method which is used in conjunction with the implant apparatus and methodology of the invention. In FIG. 12, an implant having a head 10A and bottom 11A is held in position in opening 79 formed in alveolar bone by a solidified hydroxyapatite composition 28. Composition 28 solidified when the surrounding alveolar bone 80 grew into the composition 28 in opening 79. Head 10A has a conical head which tapers upwardly from body 11A toward the gum tissue 81. Head 10A has outer smooth continuous surface 13A. Body 11A includes outer smooth continuous surface 14A. Frustoconical support member 70 is attached to head 10A. Sacrificial frustoconical coping 71 is slid over member 70. Sacrificial frustoconical coping 74 is slid over member 73. If desired, copings 71 and 74 can be metal and not be sacrificial. Member 73 is attached to the head 10A (not shown) of another implant (not shown) in the alveolar bone 80. Rubber, silicone, or some other acceptable material is used to form a negative mold 72 extending over and around copings 71 and 74 in the manner shown in FIG. 12. The use of such molding materials in dentistry is well known and will not be discussed herein. The negative mold includes upstanding hollow conical member 85; frustoconical hollows 83 and 84 which conform and adhere to copings 71 and 74, respectively; and, surfaces 86 and 87 which conform to gum tissue 81. When the negative mold 72 is removed from members 70 and 73, copings 71 and 74 are removed with and are imbedded in the mold 72.

Figure 14:
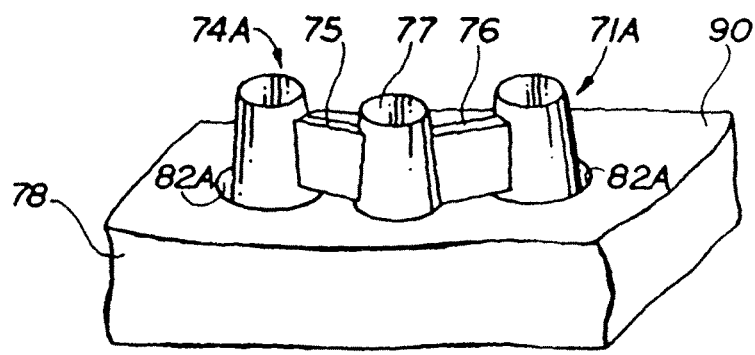
FIG. 14 is a perspective view illustrating another step in the molding procedure of FIG. 12.
Figure 15:
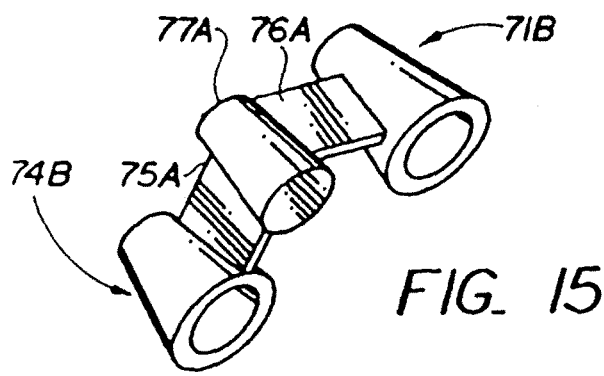
FIG. 15 is a perspective view illustrating a finished dental bridge produced according to the method of FIGS. 12 and 14.

After mold 72 has set and is removed from members 70 and 73 and from the patient's mouth, mold 72 is used to make a positive stone mold 78. This is, as is well known, accomplished by inverting mold 72, place mold 72 in a container which circumscribes mold 72, and by pouring a stone mold slurry into sacrificial copings 71 and 74 and over surfaces 86 and 87. After the stone mold slurry hardens to form mold 78, the mold 78 and mold 72 are heated until mold 72 melts and flows off of stone mold 78, or, mold 72 can simply be peeled off of the hardened stone mold with or without copings 71 and 74. The positive stone mold 78 which remains replicates the gum line 81, support members 72 and 73, and the upper portion of each head 10A as shown in FIG. 12. The stone mold 78 also replicates 82A the conical groove or detent 82 formed around the upper portion of each implant head 10A. In FIG. 14, each conical groove 82 has a shape and dimension equal to the shape and dimension of conical groove 82 in FIG. 14. Also, in FIG. 14, the portions of the stone mold which replicate frustoconical members 70 and 73 are not visible because new sacrificial copings 71A and 74A have been slipped over said portions of the stone mold (or the copings 71 and 74 which were originally used in the mouth to make mold 72 can remain on said portions of the stone mold). While the shape and dimension of each coping can vary, in FIGS. 12 to 14, each coping 71, 74, 71A, 74A is of equivalent shape and dimension. The shape and dimension of each support member 70 and 73 can also vary as desired. In FIG. 12, however, each frustoconical support member 70 and 73 is of equal shape and dimension.

In FIG. 14 a pontic comprised of frustoconical support member 77 and ribs 75 and 76 has been constructed above the upper surface 90 of stone mold 78. The pontic interconnects sacrificial copings 71A and 74A and is positioned adjacent surface 90. The pontic is typically constructed from wax, but any other desired material can be utilized. Once the construction of the pontic is completed, the sacrificial bridge support of FIG. 14 is removed from mold 78 and mold 78 is discarded, or, mold 78 is retained for use in subsequent porcelain work. After the sacrificial bridge support is removed from mold 78, its shape and dimension and appearance is identical to that of the finished metal bridge support pictured in FIG. 15.

In the next step of the molding process, the sacrificial bridge support is submersed or "invested" in a stone mold slurry and, before or as the slurry hardens, a small escape channel is formed which leads from the sacrificial bridge support through and to the upper surface of the slurry. After the stone mold slurry hardens, it is heated to melt the wax pontic and the sacrificial copings 71A and 74A. The melted wax and melted materials from the copings 71A and 74A flows out of the stone mold through the escape channel. After all of the melted material flows out of the stone mold, a hollow exists in the stone mold which is a negative of the sacrificial support bridge of FIG. 14 and of the bridge of FIG. 15. The investment molding process is continued by pouring molten metal through the escape channel into this hollow and allowing the metal to harden. After the metal hardens, the finished support bridge of FIG. 15 has been formed in the stone mold. The stone mold is broken away from the bridge to free the finished bridge from the mold. Porcelain or another desired material is placed on the bridge supports 74B, 77A, and 71B to build artificial teeth on the bridge. Ordinarily, a single artificial tooth is built on each bridge support. After artificial teeth are constructed on the bridge supports, the bridge is inserted in the patient's mouth by placing hollow support 71B over member 70 and by placing hollow support 74B over member 73. Supports 74B and 71B can be glued or otherwise affixed to members 73 and 70, respectively.

Figure 16:
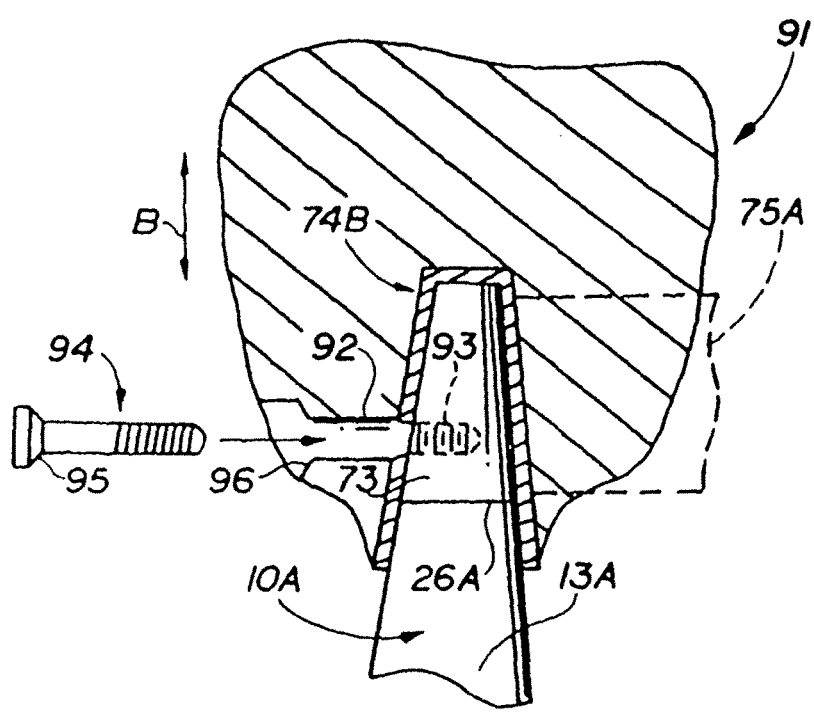
FIG. 16 is a side partial section view illustrating an artificial tooth removably attached to an implant apparatus.

A method of removably attaching a bridge support 74B and artificial tooth 91 to a member 73 is illustrated in FIG. 16. In FIG. 16 a fastener 94 is inserted into aperture 92 and threaded into internally threaded aperture 93 in member 73. Precise alignment of apertures 92 and 93 is not required because the diameter of aperture 92 is slightly larger than that of aperture 93. The undersurface 95 of fastener conforms to and bears against a portion of conical surface 96 to prevent the tooth 91 from moving in the directions of arrows B. When fastener 94 is removed from apertures 92 and 93, coping 74B can be pulled upwardly off of and free from support member 73.

In FIG. 16, the upper distal end 26A of head 10A contacts the bottom of support member 73. The outer peripheral conical surface of head 10A is contiguous with and lies in a common conical plane with the outer conical surface 13A of head 10A. Coping 74B conforms to surface 13A and to the outer conical surface of member 73 so that coping 74B slidably engages and fits said conical surfaces in the manner illustrated in FIG. 16. The co-planar relationship of the conical surface of member 73 and the conical surface 13A of member 10A is important in the practice of the invention because it enables coping 74B and tooth 91 to extend sealingly downwardly below the gum line, i.e. to extend downwardly below end 26A.

Members 70 and 73 can be fabricated from metal or from plastic, rubber, copolymer, polymer, composites, or any other desired material, as can the sacrificial copings 71, 74, 71A, 74A.

The implant method and apparatus of the invention have several advantages. First, since the opening which is formed in the bone to receive the implant does not have to conform to the shape and dimension of the implant, special drills are not necessary when the opening is formed in the alveolar or basal bone to receive the implant. Second, drilling an opening in the bone which is larger than and does not conform to the shape and contour of the implant decreases the amount of heat generated during the drilling process. This is important because bone is damaged when exposed to heat in excess of 130 degrees centigrade for one minute or more. Conventional implants require that a cylindrical opening be drilled in the bone. Drilling such openings requires the use of internally irrigated slowly rotating burrs and is more likely to generate heat which damages the bone adjacent the cylindrical opening. When an opening is drilled for the implant of the invention, a higher speed externally irrigated burr can be utilized. Third, the implant of the invention permits non-resorbable hydroxyapatite to be utilized to fill in the opening around the implant. The non-resorbable hydroxyapatite produces a strong, tough structure which is less likely to have saucerization. Saucerization occurs when bone is lost from around the implant due to stress or bacterial invasion. This use of non-resorbable hydroxyapatite is particularly advantageous when a bone ridge which has receded is being augmented to duplicate the original shape and size of the ridge. Fourth, the lateral insertion of an implant in the manner illustrated in FIGS. 6 and 7 is useful in the case where a tooth has been missing for some time and adjacent teeth have migrated into and partially filled the space of the missing tooth. When this occurs, conventional implants either are forced to be so small that they are weak or are prevented from being utilized due to the small size of the space remaining between the adjacent teeth. The implant of FIGS. 1 and 8 solves this problem because it has a large base with a thin neck which can extend between the remaining adjacent teeth. Fifth, the implant method of the invention covers the junction between a support member 70 and the head 10A (FIG. 12) of the implant. In conventional implants, this junction is exposed to oral fluids and can corrode and fail. Further, dentists often do not screw or otherwise install member 70 snugly against the top of head 10A, leaving a septic gap. Sixth, the implant of FIGS. 1, 8 and 12 can be long or short and still provide a large outer surface area for anchoring the implant in the alveolar or basal bone.

Figure 17:
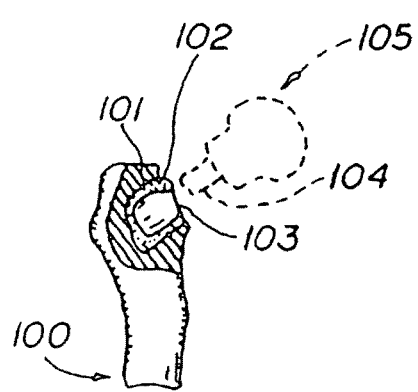
FIG. 17 is a side partial section view illustrating a hip implant procedure.

As would be appreciated by those of skill in the art, the implant methodology described above in connection with dental implants can be utilized to carry out implants in bone throughout the body. For example, in FIG. 17, the "ball" at the top of femur 100 has been removed and an oversized opening 101 has been formed in the top of femur 100. Implant 103 is inserted in opening 101. The lower portion of implant 103 is the body thereof and the upper portion of implant 103 (the portion nearest artificial "ball" 105) is the head of the implant 103. Each implant in the prior art and illustrated herein includes a lower portion, or body, and an upper portion, or head. A hydroxyapatite (HA), hydroxyapatite cement (HAC) or other composition 102 is packed around implant 103 to secure implant 103 in opening 101. An internally threaded cylindrical aperture (not visible) is formed in implant 103 to receive the externally threaded end 104 of an artificial "ball" 105. It is advantageous to form opening 101 by laterally cutting or drilling into the top of femur 100 in the manner illustrated in FIG. 6. This reduces the amount by which the femur has to be laterally displaced away from the hip socket during formation of opening 10, thus reducing trauma to surrounding nerves, muscles, blood vessels and soft tissue.

Figure 18:
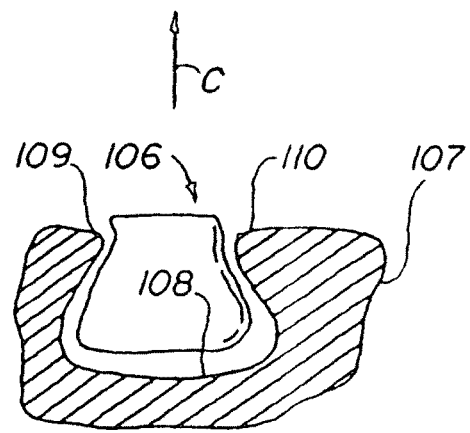
FIG. 18 is a partial side section view illustrating an interlocking opening formed in bone during an implant procedure according to the invention; and, FIGS. 19 to 21 illustrate an alternate implant procedure in accordance with my invention.

In FIG. 18, the opening 108 in bone 107 and the implant 106 are shaped and dimensioned such that when implant 106 is laterally slid into opening 108, a mechanical lock is formed and implant 106 cannot be removed from opening 108 in the direction of arrow C. Similarly, opening 108 and implant 106 can be formed such that implant 106 is inserted in opening 108 in the direction directly opposite that of arrow C and is rotated 90 degrees about an axis parallel to arrow C such that after implant 106 is so rotated, it cannot be displaced out of opening 108 in the direction of arrow C because the longer dimension of implant 106 has been turned to a position similar to that shown in FIG. 18 under the inwardly extending lips 109 and 110 of opening 108.

The opening 108 illustrated in FIG. 18 can be formed and an implant inserted in opening 108 which flares outwardly like implant 106 but which can be readily withdrawn from opening 18 in the direction of arrow C. The implant is anchored in opening 108 by packing HA, HAC, or another composition in opening 108 and around implant 106. The composition 102 used to pack around an implant 103 can include magnetic fibers and have a viscosity which permits the fibers to align when a magnetic force is applied to the composition. The composition 102 can also, in combination with the magnetic fibers or in place of the magnetic fibers, include fibers which do not respond to the magnetic force.

As noted earlier, active compositions can be utilized in combination with or in place of hydroxyapatite compositions. Such active compositions, or tissue growth factors, can be intermixed with hydroxyapatite or other materials utilized as packing around an implant, can be coated on an implant 103, or can be inserted in situ intermediate the implant 103 and opening 101 to cause, for example, the bone to grow back inwardly toward the implant. In the event implant 103 is coated with a bone growth factor or a bone growth factor is inserted in situ intermediate an implant 103 and opening 101 in the bone, positioning means can be utilized to maintain implant 103 in its desired position in opening 101 until bone ingrowth contacts implant 103 and maintains it in position. The positioning means can also be utilized to maintain an implant in position until a filler material is packed in opening 101 around the implant to anchor the implant in position. Such positioning means can consist of a collar or template which fixedly and/or resorbably contacts or supports implant 103 and is anchored to surrounding bone or other tissue. The positioning means can also consist of a putty or gel which is packed around the implant 103 to maintain it in position while bone grows into the putty or gel and to the implant or until the putty or gel sets up. Once bone ingrowth secures implant 103 in its desired position, the collar or template which is used to support the implant is removed or is resorbed. Resorption of the collar or implant can occur according to the natural physiological process of the body or can be triggered and/or facilitated by external means such as heat, electricity, enzymes injected into tissue, etc.

By way of further example of the template just referred to, an implant to replace a missing first molar in the lower jaw of a patient is carried out as follows. First, the space between the second premolar and the second molar which bounded the missing first molar may be laser scanned or an impression taken to define the space so that the shape and dimension of the tooth which will fill the space can be defined. An impression is taken of the lower teeth and a plaster model of the lower teeth is made using well known molding techniques. This plaster model, as does the patient's mouth, includes on open spot which at one time was occupied by the patient's missing first molar. A model is made of the artificial tooth which will be mounted on the implant. The model is properly positioned in the open spot in the plaster model and a impression is made of the plaster model using plaster, plastic or any other desired material. This plastic model will fit over and conform to the lower teeth in the patient's mouth. An opening is formed through the plastic model and an externally threaded screw or other attachment means is attached through and extends downwardly from the plastic model so that the implant which will be utilized in the mouth of the patient can be detachably secured to the externally threaded screw. The externally threaded screw positions the implant in the exact desired orientation, both laterally and vertically, with respect to the plastic model and with respect to the opening formed in bone in the patient's mouth (or with respect to bone in the patient's mouth on which the implant is set). An oversized opening 27 (FIG. 3) is drilled in the alveolar bone. The bottom of the opening is prepacked with a selected amount of hydroxyapatite or other composition. The implant 11 is threaded onto the externally threaded screw in the plastic model and the plastic model is fit over the crowns of the patient's lower teeth to force the implant 11 into the opening 27 and force the hydroxyapatite composition up and around the implant 11. Openings can be formed in and through the plastic model to permit hydroxyapatite composition to be added to or removed from opening 27. Or, in the event implant 11 is simply coated with a bone or tissue growth factor, openings need not be formed through the plastic model to permit access to opening 27 because the plastic model positions the implant 11 in the exact desired location in opening 27 and maintains the implant 11 in that position until the tissue growth factor causes an outgrowth of new bone from opening 27 which contacts and anchors implant 11 in position. The coating of bone or tissue growth factor can occur just prior to insertion of the implant, after the implant is inserted, or well prior to insertion of the implant. After the implant 11 is anchored by the growth of new bone toward the implant, the externally threaded screw is turned out of the implant, the plastic model is removed and an artificial tooth can be threaded into or otherwise attached to the anchored implant 11. After (of before, if desired) the artificial tooth is attached to implant 11, a tissue growth factor can be applied around the implant to the surface of the implant, to the surface of bone around implant 11, or to gum tissue to promote the growth of gum tissue over the surface of the bone and adjacent the artificial tooth.

Growth factors can be utilized to induce the growth of "hard tissue" or bone and "soft tissues" like ectodermal and mesodermal tissues. As used herein, the term growth factor encompasses compositions and living organisms which promote the growth of hard tissue, such as bone, or soft tissue in the body of a patient. The compositions include organic and inorganic matter. The compositions can be genetically produced or manipulated. The living organisms can be bacteria, viruses, or any other living organism which promote tissue growth. By way of example and not limitation, growth factors can include platelet-derived growth factor (PDGF), epidermal growth factor (EGF), fibroblast growth factor (acidic/basic)(FGF a,b), interleukins (IL's), tumor necrosis factor (TNF), transforming growth factor (TGF-B), colony-stimulating factor (CSF), osteopontin (Eta-1 (OPN), platelet-derived growth factor (PDGF), interferon (INF), bone morphogenic protein 1 (BMP-1), and insulin growth factor (IGF). Recombinant and non-recombinant growth factors can be utilized as desired. Bacteria or viruses can, when appropriate, be utilized as growth factors. For example, there is a bacterial hydrophilic polypeptide that self-assembles into a nanometer internal diameter pore to build a selective lipid body. Various enzymes can be utilized for the synthesis of peptides which contain amino acids that control three-dimensional protein structure and growth. Growth factors can be applied in gels or other carriers which regulate the rate of release of the growth factors and help maintain the growth factors, and the carrier, at a desired location in the body. Time release capsules, granules, or other carriers containing growth factor can be activated by tissue pH, by enzymes, by ultrasound, by electricity, by heat, by selected in vivo chemicals or by any other selected means to release the growth factor. The carrier can be resorbable or non-resorbable. Or, the growth factor itself can be activated by similar means. Either the carrier or the growth factor can mimic extracellular fluid to control cell growth, migration, and function. The growth factor can be administered orally, systemically, in a carrier, by hypodermic needle, through the respiratory tract, or by any other desired method. The growth factor can also be administered into a capsule or other man-made composition or structure placed, in the body. While administration of the growth factor is presently usually localized in the patient's body, circumstances may arise where it is advantageous to distribute a growth factor throughout the patient's body in uniform or non-uniform concentrations. An advantage to growth factors is that they can often, especially when in capsule form or in some other containment system, be inserted to a desired site in the body by simply making a small incision and inserting the growth factor. The making of such a small incision comprises minor surgery which can often be accomplished on an out-patient basis. The growth factors can be multifactorial and nonspecific.

A variety of collagen materials can be used alone and in combination (Types 1 to 12) to form a containment sock, pocket or other structure for a growth factor, which structure may have useful features of controlled degradation and porosity for tissue reconstruction. Other known naturally occurring materials such as biopolymers, cross-linked protein scaffolds, and gels can be used alone or in combination with each other or with any other material to form a containment system for hydroxyapatite or other tissue augmentation materials. A containment pocket or other structure can be formed with synthetic organic materials such as polymers or plastics, with natural inorganic materials (e.g., hydroxyapatite and other ceramics), with organic materials (e.g., biopolymers), or with synthetic inorganic materials.

Possible polymers usable in a pocket or other containment structure constructed in accordance with the invention include, without limitation, poly(Amides), poly(Esters), poly(Orthoesters), poly(Anhydrides), poly(Ureas), poly(Orthoesters), poly(Anhydrides), poly(Ureas), poly(Alkyl 2-Cyanoacrylates), poly(Dihydropyrans), poly(Acetals), poly(Phosphazenes), and poly(Dioxinones). Each of the foregoing polymers is biodegradable in natural systems by undergoing a hydrolytic, enzymatic, or other breakdown or degradation and, as such, is capable of providing biodegradable matrices, scaffolds and other useful structures of a containment structure. Examples of biodegradable polyamides include glutamic acid, glutamic acid/leucine, biodegradable nylon, glutamic acid/ethyl glutamate, hydroxyalkyl-L-glutamine, and collagen. Examples of biodegradable polyesters include D, L lactic acid, glycolic acid/lactic acid, L-lactic acid, caprolactone/D,L lactic acid, diglycolic acid/transcyclonhexanedimethanol, and polyesterhydrogels.

In one embodiment of the packing material 102 used in the invention, hydroxyapatite is mixed with a biodegradable polymer, with or without a growth factor impregnated therein, to provide a composition which resists penetration by epithelial tissues but which promotes growth of adjacent bone or soft tissue structure.

In a further embodiment of the invention, a pocket or other containment structure is fabricated from a microporous material containing a drug or other agent in its pores which promotes the growth of living tissue. The pore sizes can be in the range of 25 to 400 microns, or can have any desired size. The containment structure can be positioned in an opening 101, adjacent selected soft tissue or bone, or at any other location in the patient's body.

In another embodiment of the invention, hydroxyapatite or another tissue augmentation material is mixed with a material to produce a mixture which is sensitive to ultraviolet light and which hardens and sets after being dispensed at a desired location intermediate the tissue and underlying bone. UV light is delivered by fiber optic means to the location at which the augmentation material is dispensed intermediate tissue and underlying bone. The UV light promotes the hardening or setting up of the tissue augmentation material.

In still another embodiment of the invention, a volume of tissue augmentation material is provided with a coating which resists migration from the tissue augmentation material of tissue augmentation drugs or other growth factors or materials. The coating can be biodegradable and break down over time.

The hydroxyapatite (HA) and hydroxyapatite cement (HAC) compositions which can be utilized to pack around implants in accordance with the invention are inorganic, crystalline materials. The hexagonal rhombic prism structure and calcium and phosphate composition of HA's and HAC's are very similar to the natural ceramic hydroxyapatite mineral that makes up the inorganic portion of bone and teeth. HA's and HAC's are bioactive and interact with bone and teeth by forming a direct physicochemical bond with these hard tissues. Consequently, HA's and HAC's are osteoconductive and initiate bone ingrowth. HA's and HAC's can also harbor osteoinductive material like osteocalcin which helps form new bone cells. A distinct advantage of HAC's is that they can, while still in a relatively low viscosity state, be interposed between an implant and opening in the bone to readily conform to implant and bone surfaces. Neither HAC's or HA's generate any appreciable heat when used to pack around an implant. HAC's and HA's can be mixed with bodily fluids.

HAC'S, HA's, growth factor compositions, and other packing compositions used to pack around an implant can be formulated to expand after being inserted intermediate an implant and surrounding bone. Such expansion is advantageous because after an opening is cut in bone, the bone adjacent the opening tends to shrink "away" from the opening, enlarging the opening. By way of example, an HAC packing composition can be formulated to expand by intermixing a gas generating material or a material with a thermal coefficient of expansion with the packing composition. The gas generating material forms pores in the packing composition and causes it to expand. The gas generated is preferably carbon dioxide, nitrogen, or another inert gas is preferred. The gas generating or expandable material can be resorbable. If desired, the packing composition can be aerated with a gas before it is inserted in an opening to anchor an implant in place. Polyethylene has a coefficient of thermal expansion of about 0.00018 per degree Centigrade. Polyethylene or another polymer material with a preferred coefficient of thermal expansion can be utilized as a component in the packing composition. Or, the packing composition can include a liquid component which expands when the liquid component sets and solidifies.

In one embodiment of the invention, a dental implant and crown are designed to custom fit in the alveolar bone and efficiently dissipate occlusal stress generated during use of the crown to chew food. Implants other than dental implants can also be designed using the following principles.

A ruler, X-ray, laser scanner, impressions of the teeth and jaws, or other means are used to define the shape and dimension of the space to be occupied by the artificial crown which is attached to the implant and to define the shape and dimension of the alveolar bone in or on which the implant is to be positioned. A force diagram can be generated which defines how the roots of each original tooth in the mouth of an individual dissipate the stresses generated on the tooth during chewing and/or biting. Similarly, a force diagram can be generated defining an optimal root design for uniformly dissipating stress into alveolar bone, for dissipating more stress into stronger areas of the alveolar bone, etc. Such an optimal root design is ordinarily arrived at with the use of a computer and is important because many dental problems derive from the interaction of teeth with bone surrounding the teeth. The quality of the bone adjacent teeth varies. Some bone can withstand occlusal stress better than other bone. Some areas of the jaw have more alveolar bone adjacent to and supporting a tooth than do other areas of the jaw. Another factor which can be utilized to determine the optimal shape and dimension of the implant (and crown) is the material used to fabricate the implant.

An eight foot long two inch by four inch piece of lumber better resists a force which is applied perpendicular to the length of the lumber and to a two inch side of the lumber than it resists the same force applied to a four inch side of the lumber and perpendicular to the length of the lumber. Similarly, the orientation of an implant root with respect to the surrounding bone can have a bearing on the ability of the root and the implant to resist a force vector which is applied to the implant at a particular point and at a particular orientation. Therefore, the orientation of the roots of the implant is another factor which can be taken into consideration by a computer in designing the optimal implant. Still another factor is the shape and position of the tooth (or teeth) which opposes and will contact the crown on the implant after the implant and crown are anchored in alveolar bone.

In the dental implant art, the "Theory of Available Bone" teaches that implants are customized to fit in existing bone. The preferred method of the invention directly contradicts the Theory of Available Bone because the method of the invention teaches optimizing the effectiveness of an implant by first defining the optimal shape and dimension and the density or other physical properties of the bone which should be available to anchor the implant. In the method of the invention, if a sufficient volume of bone is not available, additional bone volume is generated by packing HA, HAC or some other material on existing bone to generate new bone, by using growth factors to generate new bone, or by using any other desired procedure to generate new bone. If the density of the existing bone is not sufficient, existing bone can be removed and replaced with HA, HAC, or another desired composition which will have the desired density or other physical properties or which will cause new bone to grow which has the desired density or other physical properties. HAC can form bone consisting of about 77% by weight mineral composition. This is denser than natural bone and can be particularly desirable in forming new bone in the posterior bone areas of the mouth. The bone in the posterior areas of the mouth supports the molars. Such bone typically is less dense than the bone in the anterior areas of the mouth. Bone in the anterior areas of the mouth supports incisors. In addition, if the existing bone volume is too great, bone can be removed; for example, a bone spur could be removed. Consequently, the method of the invention propounds a "Theory of Optimal Bone—Optimal Implant" design and implementation in which existing bone structure can be altered and the design of each implant can, if appropriate, differ from the design of the other implants in a patient's mouth in order to insure that a implant is formed which effectively distributes the occlusal forces generated on the implant and bone during use of the teeth. Any desired set of criteria or parameters can be used in defining the desired volume, density, and other physical properties of the bone used to support an implant. For example, but not by way of limitation, the volume of bone typically will approximate the volume of the original bone structure which is (or was) present in the mouth when the patient is a young adult.

Such bone volume is readily measured or, in the event portions of the original bone structure have been lost, can be readily approximated. The desired density of the bone typically presently will be at least equal to the density of the original bone structure. Further, by way of example, the largest possible bite force is not necessarily produced in a direction which is perpendicular to the occlusal plane. The posteriorly and medially directed forces generally reach higher values than the anteriorly and laterally directed forces, respectively.

A computer can also be utilized to determine the position of the implant at which the implant optimally distributes stresses into surrounding bone. The optimal position of the implant can be determined based upon selected factors included, but not limited to, the morphology of the surrounding alveolar bone, the size and stability of adjacent teeth, etc. For example, once the shape and dimension of an implant is determined, the implant may better distribute stress if it is positioned in (or on) alveolar bone closer to a first adjacent tooth than to a second adjacent tooth because the quality of bone is better near the first adjacent tooth.

The shape and dimension of the crown can depend on factors including, but not limited to, the type of tooth (a molar has more cusps than an incisor), the size of the space in the patient's mouth in which the crown must fit, and the material used to fabricate the crown (a stronger material might enable portions of the crown to be smaller than if a weaker material is used).

After the shape and dimension of the implant and crown are defined, the implant and crown can be manufactured using computerized equipment. A computerized lathe system could, for example, be used to cut the implant from a piece of metal and to cut, mold, or otherwise form the crown which is secured to the implant. Or, the implant and crown can be produced utilizing any desired conventional production methods. After the implant and crown are produced, the implant is anchored at the desired position in the alveolar bone using any of the procedures earlier described. For example, on opening can be formed in the alveolar bone, the implant inserted in the opening, and HA or other material packed around the implant to anchor the implant in the opening. The crown can be attached to the implant before or after the implant is secured in the alveolar bone.

Locating an implant in the upper molar area of the mouth can be difficult because the alveolar crestal bone is thin and adjacent the sinuses. Consequently, the mass or volume of available bone in which to anchor an implant is marginal. In order to position an implant in the alveolar crestal bone in the upper jaw, a first prior art procedure was developed. In this first prior art procedure, the alveolar bone is scored along a rectangular line. The portion of the alveolar bone circumscribed by the score line, referred to herein as the "pad", is then carefully pushed inwardly to avoid tearing the Schneiderian membrane and to form a rectangular opening through the alveolar bone. A block-shaped base is inserted through the rectangular opening in the alveolar bone to a position in which the base contacts or is adjacent the pad. The area around the base is filled with loose hydroxyapatite material and the opening in the alveolar bone is covered with the gum or another material to permit the hydroxyapatite to harden. Six to nine months later, the gum is reopened to anchor an implant and/or artificial crown in the block-shaped base.

The foregoing first prior art procedure for positioning an implant in the molar alveolar bone has several disadvantages. First, avoiding rupture of the Schneiderian membrane is sometimes difficult, which means there is an increased risk that infection in the patient's sinus will spread into the hydroxyapatite or other areas of the graft. Second, the block-shaped base must be covered, or buried, while the hydroxyapatite hardens. This means a second later operation is required to insert an artificial crown or implant in the base once the hydroxyapatite hardens. Third, the insertion of an implant is postponed for six to nine months while the sinus graft heals. Fourth, the block-shaped base tends to shift out of its desired position adjacent the pad, which makes it difficult, if not impossible, to properly position the implant when the gum is later reopened and the implant is inserted in the block-shaped base.

A second prior art procedure, termed the lateral sinus lift procedure, was developed to overcome shortcomings in the first procedure discussed above. In this second prior art procedure, a cut is made through the maxilla, exercising care not to rupture the Schneiderian membrane. The cut forms a flap which is displaced, or lifted, laterally and upwardly into the sinus cavity, again without rupturing the Schneiderian membrane which lines the sinus cavity. Avoidance of damage to the Schneiderian membrane during the lateral sinus lift is important because rupture of the membrane permits the rapid spread of infection in the sinus cavity. In the event the Schneiderian membrane is ruptured, a resorbable collagen pad is used to cover the rupture, or the rupture is otherwise repaired. After the flap is lifted, the space intermediate the flap and the alveolar crest is filled with porous hydroxyapatite. Six months later, an opening, i.e., an osteotomy, is carefully drilled through the alveolar crest and into the hardened hydroxyapatite. The opening closely conforms to the shape and dimension of an implant which is fitted into the opening.

The foregoing second prior art procedure for positioning an implant in the molar alveolar bone has several disadvantages. First, avoiding rupture of the Schneiderian membrane is sometimes difficult, which means there is an increased risk that infection from the sinus will spread into the graft. Second, the incision through which the hydroxyapatite is inserted must be sealed. Third, the insertion of an implant is postponed for six months while the sinus graft heals. This means a second operation is required to insert the implant. Fourth, the insertion of the implant requires the formation of an opening which closely conforms to the shape and dimension of the implant.

A third prior art procedure for positioning an implant adjacent the sinuses is similar to the second prior art procedure described above in that a lateral sinus lift is also performed. However, in the third prior art procedure, after the lateral sinus lift is performed an opening is carefully drilled through the alveolar crest. This opening conforms to and receives the upper portion of an implant. Since the alveolar crest is thin, the lower portion of the implant extends from the alveolar crest into the space intermediate the alveolar crest and the flap of bone bent inwardly during the lateral sinus lift. Hydroxyapatite is then packed between the alveolar crest and the flap of bone and is packed around the implant.

The foregoing third prior art procedure for positioning an implant in the molar alveolar bone has several disadvantages. First, avoiding rupture of the Schneiderian membrane is sometimes difficult, which means there is an increased risk that infection will travel from the sinus into the graft. Second, gum tissue must be used to cover, or bury, the implant while the hydroxyapatite solidifies. This necessitates a later operation to expose the implant to attach an artificial crown to the implant. Third, the insertion of the artificial crown in the implant is postponed for six months while the sinus graft heals. Fourth, the insertion of the implant requires the formation of an opening which closely conforms to the shape and dimension of the implant.

Figure 19:
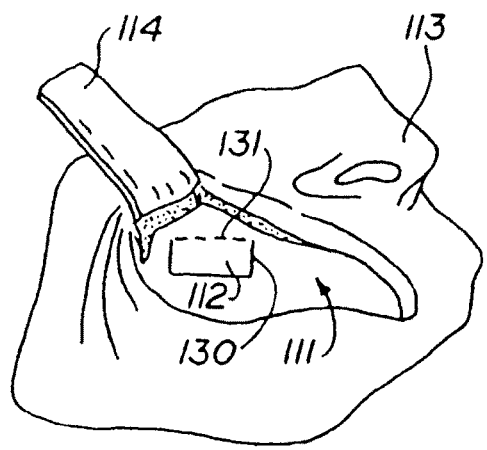
Figure 20:
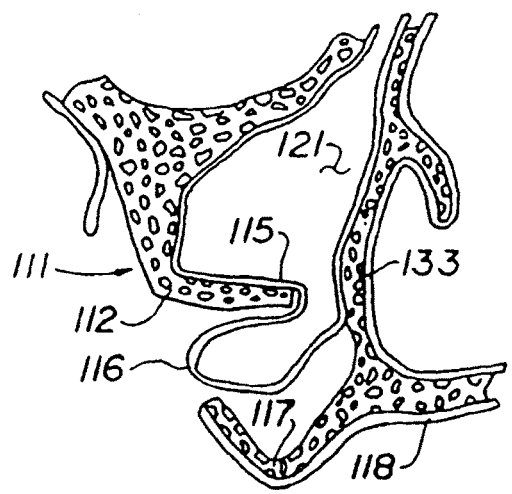
Figure 21:
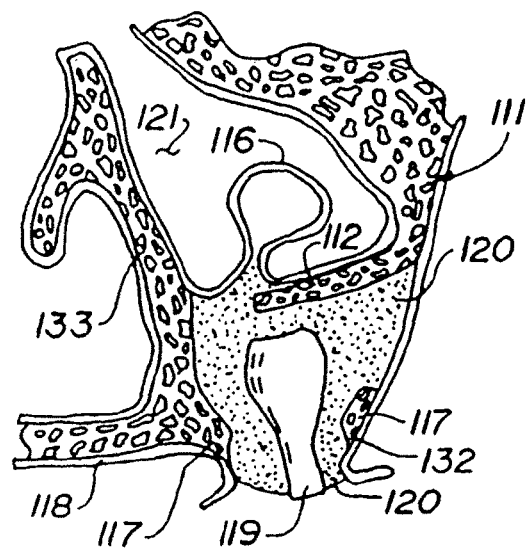

One method of the implant of the invention facilitates the insertion of an implant in the alveolar crest adjacent the atrophic posterior maxilla. This method of the invention is illustrated in FIGS. 19 to 21. In FIG. 19, a retractor 114 is utilized to draw soft tissue away from the posterior maxilla 111. A drill or other tool is used to cut through the maxilla 111 to form a rectangular groove 130 defining a flap 112. If necessary, the maxilla 111 can be scored along line 131 to facilitate the inward and upward bending of flap 112 into sinus cavity 121 to the position illustrated FIG. 20. An opening 132 is formed through the alveolar bone 117. An implant 119 is inserted through opening 132 into the area intermediate flap 112 and the alveolar bone 117. Hydroxyapatite cement (HAC) 120 is used to pack around implant 119 intermediate flap 112 and bone 117. The HAC is inserted through opening 132 or through the opening formed in the maxilla when flap 112 is bent upwardly and inwardly into the sinus cavity 121. If desired, the Schneiderian membrane can be scraped away from and off of the bone to facilitate bonding of the HAC with the bone. The HAC has a putty like consistency and rapidly sets up and hardens, typically within 10 to 15 minutes. When the HAC hardens, it seals the sinus cavity 121. Sealing the sinus cavity 121 is critical because bacteria in the sinus cavity 121 which may invade the graft through a breach in the Schneiderian membrane are sealed in the sinus cavity. Consequently, the method of the invention permits the Schneiderian membrane to be cut through, enables an implant to be quickly placed adjacent the maxilla, and does not require the formation through the alveolar bone (or hardened HAC) of an opening which closely conforms to the implant being utilized. The orientation of implant 119 can, until HAC 120 hardens, be adjusted by canting or tilting implant 119 in opening 132 and in the area intermediate flap 112 and bone 117. HAC is presently preferred in the practice of this method of the invention because it includes hydroxyapatite and because it rapidly sets up. Any other desirable packing material can, however, be utilized in place of HAC. Various other packing materials are discussed earlier herein.

The method of the invention may enable an implant and crown to be completely installed in one operation. In contrast to the prior art procedures described above, the method of the invention does not require that an initial incision be made, be closed, and then be reopened at a later date to complete the implant procedure. In the method of the invention, the implant and/or artificial crown attached to the implant can extend through the gum into the mouth soon after an opening is formed through alveolar bone and after the Schneiderian membrane is ruptured.

The method illustrated in FIGS. 19 to 21 can also be carried out without forming flap 112. In this procedure, opening 132 through the alveolar bone 118 is formed and HAC putty is packed between the maxilla 111 and other bone 133 bounding the sinus cavity 121. The implant 119 is positioned in the HAC. If desired, the entire sinus cavity 121 can be filled with HAC or another packing material. Again, if desired, the implant and/or artificial crown attached to the implant can extend through the gum into the mouth.

In another embodiment of the invention, genetically produced living material is used to form an implant in the bone of a patient. The DNA structure of a patient is analyzed from a sample of blood or other material extracted from a patient and a biocompatible tooth bud 122 (FIG. 3) is produced. The bud 122 is placed in an opening 123 in the alveolar bone and packing material is placed around or on top of the bud 122. The size of opening 123 can vary as desired. The packing around bud 122 can comprise HAC 124, hydroxyapatite, blood, growth factors, or any other desirable packing material. The bud 122 grows into a full grown tooth in the same manner that tooth buds which are in the jaws of children beneath baby teeth grow into full sized teeth. In a first variation of this embodiment of the invention, analysis of the DNA of the patient is used to identify and select in vitro the genetic material which causes the creation and growth of a tooth bud. This genetic material at least includes a gene or genes, and may include other portions of the DNA. A transcriptional activator is utilized to activate transcription of these tooth bud genes in vitro. An enhancer is used to drive the specific expression of the transcriptional activator. After the enhancer drives the expression of the transcriptional activator, the transcriptional activator transactivates the tooth bud genes. Nutrients and/or other growth factors can be used to sustain and/or promote the creation and growth of, or if appropriate, to cause the differentiation of, a tooth bud after the tooth bud genes are activated. After the tooth bud reaches a desired size, it is transplanted into the jaw bone of a patient. As used herein, the term tooth bud designates a partially grown tooth. Nutrients and/or other growth factors can be used to sustain and promote the growth of, or if appropriate, to cause the differentiation of, the tooth bud after it is transplanted into the jaw of a patient. Instead of tooth bud genes, genes which cause the morphogenesis and further growth of other organs or hard or soft tissue in the body can be identified from the patient's DNA and utilized to grow in vitro organs or tissue for transplant into the body. The organs or tissue can be partially or completely grown at the time of transplant. In a second variation of the above embodiment of the invention, the structure of the gene or genes which control the growth of a tooth bud in a human being is known, and the genetic material comprises comparable artificially produced genes, or genes harvested from other human beings or animals are transactivated to create and grow a tooth bud. Such artificially produced genes or genes from other animals are transactivated to create and grow a tooth bud in vitro, after which the bud (or other organ or tissue) is transplanted into the body of the patient. The tooth bud grows in a tooth which is comprised of dense, semirigid, porous, calcified skeletal tissue.

In another embodiment of the invention, instead of transplanting a bud 122 into the jaw of a patient, a quantity of genetically produced living material which causes bud 122 to form in the alveolar bone can be placed at a desired position in the alveolar bone such that bud 122 is morphogenetically created in vivo and grows into a full sized tooth. Instead of forming an opening 123, a needle or other means can be used to simply inject the genetically produced living material into a selected location in the alveolar bone. As would be appreciated by those skilled in the art, genetically produced materials can be inserted in the body to cause the body to grow, reproduce, and replace leg bone, facial bone, and any other desired soft and hard tissue in the body. In one variation of this embodiment of the invention, the genetic material is placed at a desired position in the alveolar bone (by, for example but not by way of limitation, forming an opening 123 to receive the genes or by utilizing a needle to insert the genes at a desired site) to create and grow morphogenetically a tooth bud and, subsequently, a tooth. The genetic material is presently preferably accompanied by a transcriptional activator to turn on the genes' expression, an enhancer to drive the specific expression of the transcriptional activator, and by nutrients and/or other growth factors which promote the in vivo creation and growth of a tooth bud and tooth. The genes can be transcriptionally activated either prior to being inserted or after insertion in the alveolar bone. Instead of tooth bud genes, genes which cause the morphogenetic creation and growth of other organs or other hard or soft tissue in vivo can be identified from the patient's DNA or from another source, and the genetic material can comprise comparable artificially produced genes or genes removed from another animal or otherwise generated. The genetic material is then inserted at desired locations in a patient's body and utilized to create and grow morphogenetically in vivo organs or other hard or soft tissue. Such genes presently preferably are accompanied by a transcriptional activator to turn on the gene's expression, an enhancer to drive the specific expression of the transcriptional activator, and by nutrients and/or other growth factors which promote the creation and growth of a tooth bud and tooth. The genes can be transcriptionally activated prior to or after they are inserted in a patient's body. Any desired substance or means can, as would be appreciated by those of skill in the art, be utilized to cause the activation or initiation of a gene or genes to express themselves by creating and growing morphogenetically an organ or other hard or soft tissue at a desired location or location(s) in the body of a patient.

The gene or genes used to create and grow morphogenetically a particular organ or other tissue in vivo or in vitro can, if desired and appropriate, be accompanied by or be connected to other genes or DNA material which does not play a part in the growth of the desired organ or other tissue.

In another embodiment of the invention, I provide a method for curing dental disease. The method comprises the step of introducing into the body a substance or form of energy which replaces or alters a gene or genes in the patient's DNA to improve the ability of the patient's to defend against, weaken, or destroy bacteria or viruses which cause dental disease. The replaced or altered genes express themselves in at least some of new cells subsequently produced by the patient's body. For example, the altered or new genes in the patient's DNA may make it more difficult for bacteria, cytokines, or bacterial antigens to penetrate the gum tissue in the mouth of a patient. The particular embodiment of the invention which is preferred is using a chemical substance, heat, electromagnetic energy, or any other means to alter the structure of an existing gene or genes in the patient's DNA or the bacteria's or virus' DNA in vivo, i.e. alters the DNA while the DNA is in the patient's body. This embodiment can be used to improve the body's capability to defend against any disease or illness and is different from current prior art methods of importing new genes which are intended to replace or supersede the original genes existing in the patient's DNA. Morphogenesis or morphogenetics is the origin and evolution of morphological characters and is the growth and differentiation of cells and tissues during development.

The HAC 120, 124 or other packing material used in the implant methods of the invention can include BIODEL or other small polymer beads or carriers of antibiotic materials.

As used herein, hydroxyapatite cement (HAC) is a cement composed entirely or in substantial part of calcium phosphate salts. HAC can be combined with water to form a dense paste which is applied and shaped intraoperatively. HAC sets in vivo in approximately 10 to 15 minutes to form a structurally stable implant composed of microporous hydroxyapatite. The calcium phosphate salts tetracalcium phosphate and anhydrous dicalcium phosphate are the primary components of HAC. These salts react in water to isothermically form hydroxyapatite. After the calcium phosphate salts in powder form are mixed with water, the resulting composition sets in about ten to fifteen minutes. The microenvironment in the set cement is saturated with calcium phosphate salts. Hydroxyapatite precipitates in situ from this microenvironment during a reaction which typically takes from four to six hours.

A further embodiment of the invention concerns the integration of a dental implant into the lower jaw of a patient. Portions of the bone comprising the lower jaw are hollow and lined with marrow or other soft tissue. A first small opening 134 (FIG. 3) can be formed through the outside of the jaw and a second small vent opening can be formed through the inside of the jaw or elsewhere. A pressurized tube or other means is used to inject hydroxyapatite cement slurry through opening 134 into the hollow area in the lower jaw. The second opening serves as a vent which permits air or other material to escape from within the lower jaw when hydroxyapatite cement slurry is injected in the jaw. If desired, the first opening can be made slightly larger than the tube used to inject HAC slurry into the jaw such that the first opening permits air or other material inside the jaw to vent outwardly through the first opening while HAC slurry flows from the tube into the jaw. In this case, the second vent opening may not be required. An X-ray(s) can be taken of the jaw to insure that the desired areas of the lower jaw are filled with HAC slurry.

After the HAC slurry is injected into the jaw, the first and second openings are plugged with HAC putty, polyglycolic acid, bone wax, or another desirable material. After the HAC slurry which was injected into the jaw hardens sufficiently, on opening can be made through the alveolar bone of the lower jaw and into the hardened HAC to receive an implant.

A HAC slurry injection method similar to the slurry injection method described above for the lower jaw can be used to inject HAC slurry into a space between the sinuses and alveolar bone of the upper jaw. A small access opening is drilled through the maxilla. Or, the Caldwell-Luc approach can be utilized to gain access to the sinus through the nose. Once access is gained to the sinus, an instrument is used to score and rupture the sinus membrane so that HAC injected into the sinus can contact and bond to the underlying bone. HAC slurry or another desirable material is then injected into the sinus through the opening with a tube or by using other means. After the HAC slurry hardens, an opening can be formed through the alveolar bone and into the hardened HAC to receive an implant. HAC slurry, injectible hydroxyapatite, or other desired materials—including but not limited to bioactive osteogenic materials—which facilitate the formation of new hard bone by the body, can similarly be injected into the "hollow" soft tissue inner marrow areas of the femur or other bones of the body through small holes formed in the bones.

Genes express themselves by creating and growing morphogenetically any organ or other hard or soft tissue. Transciptional activators turn on a gene's expression.

Transcription is the synthesis of messenger RNA (mRNA), the first step in relaying the information contained in DNA. Transcription begins as the interaction between a strand of DNA and the enzyme RNA polymerase. Enzymes can be growth factors. Various enzymes can be utilized in the synthesis of peptides which contain amino acids that control three-dimensional protein structure and growth.

In accordance with the invention, genetic material plus growth factor(s) are implanted directly or indirectly to grow, reproduce, and replace desired soft and hard tissue in the body.

The first step in making an implant is to analyze the DNA. DNA arrays (biochips) and other DNA sequencing methods are known in the art. The genetic material can includes a gene or genes and/or other portions of DNA. A transcriptional activator is utilized to activate transcription. The genetic material can be from the patient, can be artificially produced, or can come from other human beings or animals.

Genetic material is well conserved in nature. The *Drosophila* eyeless gene (ey), the mouse small ey gene (pax-6), and the Aniridia gene in humans are all homologous.

Transgenic animals have attached a promoter (a growth factor) to a specific gene. The resultant initiation of transcription produces a desired protein. For example, human growth hormone can be produced by a farm animal. Promoters are tissue specific. To produce the protein albumin, the gene for albumin is attached to a promoter that is found only in liver tissue. Once the albumin producing promoter—gene pair is inserted into the genome, albumin is produced by future generations.

The initiation of transcription in the fly *Drosophila* is caused by a transcriptional activator which is obtained from yeast and is called GAL 4. GAL 4 causes tissue specific expression in flies. An upstream gene for eye formation in a fly is ey (eyeless). A growth factor is attached to the ey gene to grow an eye. Two sets of flies are mated to produce a generation of flies having additional eyes.

The first set of flies is genetically engineered to randomly insert GAL 4 into its genome at twenty different locations.

The second set of flies is also genetically manipulated by placing in the eggs of the second set of flies the recombinant eyeless gene and GAL 4 binding sites. The eggs mature to produce flies each having the eyeless gene in every cell in the flies body.

Genomic engineering of all kinds has created an infinite range of genetic possibilities for implants and growth factors due to DNA cloning and recombinant DNA. Cis position and trans position genes are possible. In additional, annealing techniques allow DNA with DNA, RNA with RNA, or DNA with RNA. Polymerases catalyze the combining of nucleotides to form RNA or DNA. Transcription factors are DNA-binding proteins that control gene activity. Translation is the second step in the relay of genetic information. During translation, the sequence of triplets in mRNA is translated into a corresponding sequence of amino acids to form a polypeptide as the gene product. Termination codons signal the end of translation.

Antisense RNA (or DNA), cDNA's, and expression vector can be genetically manipulated or produced. The term DNA as used herein also includes mitochondrial DNA.

Genomic manipulation can also be based on locating, isolating, attaching, and manipulating single molecules. For example, the process of transcription (as seen through atomic force microscopes) has been halted by the removal of a single nucleoside triphosphate (NTP) that the RNA molecule needed for transcription. Thus, the atomic and sub-atomic levels are important in genetic engineering.

Genetic engineering can create implants and growth factors which behave in desired manners and produce selected desired results and pathways. As used herein, genetic engineering can create materials that are able to control the flow of matter and/or energy in a deliberate way by spatial, temporal, physicochemical or other physical means alone or in combination.

Desired tissues and organs can also be produced by the process of nucleation.

Genes control structure and function. A gene or a bit of genetic material may act as a master control gene which activates thousands of other genes to construct a living organ. Each one of two or more different genes can produce the same organ. For example, in *Drosophila*, the ey gene and the toy gene both are capable of eye formation.

Since genomic engineering can create a myriad of genetic possibilities, a pathway description of cellular interactions, intracellular and extracellular matrix combinations, and mitogenic or morphogenic stages is impractical.

Complex tissues and organ systems are formed through cellular proliferation and differentiation. This orderly process is regulated by peptide growth factors which are secreted locally and mediate cellular events by triggering cell surface receptors on their target cell(s).

Cells stick together, viruses stick to cells, and white blood cells stick to invading organisms. Optical tweezers developed at Bell Labs in the 1980's can measure and evaluate the "stickiness" of cells and viruses. Sticky cells can be used to attach genetic implants to selected sites. This is, for example, important when placing a soft tissue implant in or on a site of an artery wall. In this manner, an additional heart could be grown from a genetic implant. Once matured to a reasonable state, this new heart can be the body's primary heart and the old heart can be evacuated surgically. Any venous or arterial connections, reconfigurations, or ligations can be surgically attended to. Any other organ can be similarly produced at any desired site in soft or hard tissue.

Genetic implant can form a single pre cursor area and later split in two. For example, the ET gene causes two eyes to form from a single region.

Multifactorial and nonspecific cells (such as stem cells and germinal cells) can provide the necessary in vivo and in vitro cascade of genetic material once an implanted master control gene's transcription has been activated. Likewise, any host cell, cloned cell, cultured cell, or cell would work. Genetic switches (such as the insect hormone ecdysone) can be used to control genes inserted into humans and animals. These gene switches can also be used in cultured cells or other cells. Gene switches govern whether a gene is on or off making possible precise time of gene activity.

Cellular products and their derivatives can be growth factors. Viral vectors can carry and insert new genes into chromosomes. Growth factors can positively or negatively control genetic transcription. Snippets of DNA with characteristic DNA fingerprints can be used as implant materials. Transcription factor binding sites as well as receptor sites can be genetically engineered and utilized as needed. Receptor sites can also be in the nucleus of cells.

Genetic implant preferably integrate biologically into the host environment.

Murine and human genomes (and perhaps the entire metazoa) are considerably conserved at the nucleic acid and gene linkage levels.

In early tooth germ, bone morphogenic proteins BMP-2 and MPB4 regulate expression of the homeobox containing genes MSX-1 and MSX-2. These genes, along with the eyeless gene in *Drosophila* may be considered upstream genes.

The homeobox containing gene MHox regulates the epithelial-mesenchymal interactions required for skeletal organogenesis. The paired-like homeobox gene MHox is required for early events of skeletogenesis in multiple lineages.

The homeobox gene controlling the growth of kidneys has been identified.

Organs, a join capsule, a ligament, or a ligament with an organ attached can be grown at any hard or soft tissue site.

Genes express themselves by creating and growing morphogenetically any organ or other hard or soft tissue. Transciptional activators turn on a gene's expression.

Genes may also play important roles in mechanisms that control the differentiation of structures within and between organs during organogenesis.

Gap junction proteins permit the exchange of regulatory molecules between cells and play important roles during organogenesis.

EXAMPLE 1

MSX-1 and MSX-2 are the homeobox genes that control the generation and growth of a tooth. A sample of skin tissue is removed from the patient and the MSX-1 and MXS-2 homeobox gene(s) are removed from skin tissue cells. The genes are stored in an appropriate culture medium.

Germinal cells in the process of transcription are obtained from the patient by biopsy or surgical excision. The germinal cells are in hard bone tissue adjacent the apex of the immature forming root of a patient's tooth. These cells are selected because they are actively transcribing root structure and contain active growth and transcription factors which facilitate the formation of the tooth germ. The germinal cells are placed in an appropriate nutrient culture medium outside the patient's body. The homeobox genes MSX-1 and MSX-2 are added to the nutrient culture with the germinal cells. The nutrient culture is maintained at an optimum temperature, which is presently preferably 98.6 degrees F., but can be varied as desired. The homeobox genes MSX-1 and MSX-2 are permitted to bind with transcription factors in germinal cells. After the genes bind with transcription factors, the germinal cells and bound genes are replanted in the patient's body at the tooth site from which the germinal cells were harvested.

EXAMPLE 2

Example 1 is repeated, except that the homeobox genes are provided with a genetically engineered binding site for attaching to the receptor site on the transcription factor. Similar results are obtained.

EXAMPLE 3

Example 1 is repeated, except that the germinal cells are obtained from soft periodontal ligament tissue immediately adjacent the apex of the immature forming root of a patient's tooth. These cells are selected because they are actively transcribing root structure and contain active growth and transcription factors which facilitate the formation of the tooth germ.

EXAMPLE 4

Example 1 is repeated, except that the homeobox genes are provided with a genetically engineered binding site for attaching to the receptor site on the transcription factor. Similar results are obtained.

EXAMPLE 5

MSX-1 and MSX-2 are the homeobox genes that control the generation and growth of a tooth. A sample of skin tissue is removed from the patient and the MSX-1 and MXS-2 homeobox gene(s) are removed from skin tissue cells. A tooth is removed from the mouth of a patient. The tooth that was removed had an immature root structure. Transcription was occurring at the apex of the tooth that was removed. The homeobox genes MSX-1 and MSX-2 are placed at the apex of socket immediately following the extracting of the tooth. The genes bind with the transcription factor(s) and express themselves to begin the genetic cascade to form early tooth germ. The patient's body completes the formation of the tooth.

EXAMPLE 6

Example 5 is repeated, except that the homeobox genes are provided with a genetically engineered binding site for attaching to the receptor site on the transcription factor. Similar results are obtained.

EXAMPLE 7

Example 5 is repeated, except that prior to insertion of the homeobox genes in the tooth socket, tissue on the bottom of the tooth socket is loosened to expose bone cells.

EXAMPLE 8

Example 5 is repeated, except that after the tooth is pulled, add a transcription factor and energy to activate genes to initiate the formation of tooth germ.

EXAMPLE 9

Example 8 is repeated, and the transcription factor and energy activate the MSX-1 and MSX-2 genes.

EXAMPLE 10

Example 1 is repeated, except that BMP-2 and BMP-4 growth factors are obtained by recombinant or natural extraction from bone.

EXAMPLE 11

MSX-1 and MSX-2 are the homeobox genes that control the generation and growth of a tooth. A sample of skin tissue is removed from the patient and the MSX-1 and MXS-2 homeobox gene(s) are removed from skin tissue cells. The genes are stored in an appropriate nutrient culture medium.

BMP-2 and BMP-4 growth factors are obtained by recombinant or natural extraction from bone.

Living stem cells are harvested from the bone marrow, the blood of the patient, or from cell culture techniques. The stem cells are placed in a nutrient culture medium at 98.6 degrees. The temperature of the culture medium can be varied as desired but ordinarily is between 40 to 102 degrees F.

MXS-1 and MXS-2 transcription factors are obtained which will initiate the expression of the MXS-1 and MXS-2 homeobox genes.

The MXS-1 and MXS-2 transcription factors, BMP-2 and BMP-4 bone morphogenic proteins, and MXS-1 and MXS-2 genes are added to the nutrient culture medium along with the living stem cells.

EXAMPLE 12

Example 11 is repeated except that the transcription factors bind to a receptor complex in the stem cell nucleus.

EXAMPLE 13

Example 11 is repeated except that the MXS-1 and MXS-2 transcription factors are not utilized. The transcription of the MXS-1 and MXS-2 homeobox genes is activated by applying an electric spark to the nutrient culture medium.

EXAMPLE 14

Example 13 is repeated except that the stem cells are starved and the transcription of the MXS-1 and MXS-2 homeobox genes is activated by applying an electric spark to the nutrient culture medium.

EXAMPLE 15

WT-1 and PAX genes are obtained from a sample of skin tissue is removed from the patient. The genes are stored in an appropriate nutrient culture medium. PAX genes produce PAX-2 and other transcription factors.

BMP-7 and other kidney related BMP growth factors are obtained by recombinant or natural extraction from bone.

Living stem cells are harvested from the bone marrow, the blood of the patient, or from cell culture techniques. The stem cells are placed in a nutrient culture medium at 98.6 degrees. The temperature of the culture medium can be varied as desired but ordinarily is between 40 to 102 degrees F.

The WT-1 and PAX genes, and BMP-7 and other kidney BMPS are added to the nutrient culture medium along with the living stem cells.

A primitive kidney germ is produced. The kidney germ is transplanted in the patient's body near a large artery. As the kidney grows, its blood supply will be derived from the artery.

EXAMPLE 16

The Aniridia gene is obtained from a sample of skin tissue is removed from the patient. The gene(s) is stored in an appropriate nutrient culture medium.

Aniridia transcription factor (activates expression of the Aniridia gene) and growth factors (function to help stem cells differentiate during morphogenesis to form an eye) are obtained.

Living stem cells are harvested from the bone marrow, the blood of the patient, or from cell culture techniques. The stem cells are placed in a nutrient culture medium at 98.6 degrees. The temperature of the culture medium can be varied as desired but ordinarily is between 40 to 102 degrees F.

The Aniridia transcription factor and growth factors and the Aniridia gene are added to the nutrient culture medium along with the living stem cells.

A primitive eye germ is produced. The kidney germ is transplanted in the patient's body near the optic nerve. As the kidney grows, its blood supply will be derived from nearby arteries.

EXAMPLE 17

The Aniridia gene is obtained from a sample of skin tissue is removed from the patient. The gene(s) is stored in an appropriate nutrient culture medium.

Aniridia transcription factor (activates expression of the Aniridia gene) and growth factors (function to help stem cells differentiate during morphogenesis to form an eye) are obtained and added to the nutrient culture medium.

An eye germ develops. A branch of the nearby maxillary artery is translocated to a position adjacent the eye germ to promote the development of the eye germ. The eye germ matures into an eye which receives its blood supply from the maxillary artery.

The term "cell nutrient culture" as used herein can include any or any combination of the following: the extracellular matrix; conventional cell culture nutrients; and/or, a cell nutrient such as a vitamin. As such, the cell nutrient culture can be two-dimensional, three dimensional, or simply a nutrient, and is useful in promoting the processes of cellular dedifferentiation, redifferentiation, differentiation, growth, and development.

As used herein, the term "physiological nutrient culture" is a selected media(s) to control and direct an event(s) in living host system(s) (e.g., cardiovascular, pulmonary, musculoskeletal, etc.), organ(s), tissue(s), cell(s). A media is a fluid solution, gel, or quasi-solid solution (mechanical mixture) which supports and directs normal developmental pathways for cell and cell products. An event is one of the sequence of growth, division, cellular aggregation, development of cellular form, development of aggregate cellular form, secretions, etc. which lead to the development of an organ. A physiological nutrient culture can affect macromolecule(s), molecule(s), atom(s), and subatomic particle(s) in said living things. A physiolocial nutrient culture can include macromolecule(s), molecule(s), atom(s), and subastomic particle(s). A cell nutrient culture is a physiological nutrient culture. A physiological nutrient culture is not necessarily a cell nutrient culture. A physiological nutrient culture promotes cellular survival and cellular proliferation in a desired form(s) or function(s), and promotes differentiation to a selected specific function.

Growth factors control cell growth, division, differentiation, migration, structure, function, and self-assembly. Growth factors include chemical regulators and structural/mechanical regulators. Growth factors, particularly when mimicking the extracellular matrix, exert geometric and nongeometric physical, mechanical, chemical, electrical, and/or structural forces on a cell. They can change a cell's content, shape, form, and/or function. In essence, they can have a kaleidoscopic effect which is very useful in creating and promoting the growth and morphogenesis of irregularly structured cells, tissues, or complex tissues and organs such as neurons, nervous tissue, or the brain. These growth factors can activate and regulate genetic transcription.

The invention utilizes the body as an organ/tissue factory. There may, however, be occasions where the organ/tissue is completely grown ex-vivo before replant or transplant.

Physical examinations can be done on any patient to ascertain applications of the inventions herein described.

Genetic manipulation to any portion of a gene, gene(s) protein, growth factor, or cell(s) whether taken from the patient or from any other source can be done to improve organ or tissue longevity, function, or any other attribute. These materials may be synthesized in any fashion.

The extracellular matrix (ECM) may constantly change as a result of mechanical, endocrine, or genetic factors.

A nutrient package's wall thickness can be two or less nanometers, or it can be any other thickness desired. Its wall can be fabricated from protein or from any other biological or synthetic material desired.

An organ, as used herein, consists of two or more kinds of tissues joined into one structure that has a certain task. For example, the heart is an organ who job is to circulate blood throughout the body. The heart is made up of connective tissue, muscle tissue, and nervous tissue. Organ systems comprise groups of organs. A major activity in the body is performed by each organ system. For example, the digestive system comprises organs that enable the body to use food. Likewise, the nervous system includes organs that carry signals from one area of the body to another.

Genetic material comprising a portion of a gene, a gene, genes, a gene product (i.e., a composition a gene causes to be produced like, for example, an organ-producing growth factor), growth factor, or an ECM (extracellular matrix) can be used in or on the body to grow an organ or tissue. For example, the vascular epithelial growth factor gene (VEGF) or its growth factor equivalent can be inserted into the body to cause an artery to grow. When insertion of a gene, portion of a gene, gene product, growth factor, or ECM in vivo or ex vivo is referred to herein in connection with any of the implant techniques of the invention, it is understood that a cell nutrient culture(s), physiological nutrient culture(s), carrier(s), enhancer(s), promoter(s), or any other desired auxiliary component(s) can be inserted with the gene or at the same location as the gene, growth factors ECM, etc.

An artery is an organ from the circulatory system. An artery can be grown in the heart, legs, or other areas by injecting a gene or other genetic material into muscle at a desired site. Size, vascularity, simplicity of access, ease of exploitation and any other desired factors can be utilized in selecting a desired site. The gene is one of several known VEGF genes which cause the production of vascular endothelial growth factors. Several VEGF genes which produce vascular endothelial growth factors are believed to exist because nature intends for there to be several pathways (i.e., genes) which enable of the production of necessary growth factors. The existence of several pathways is believed important because if one of the genes is damaged or inoperative, other similar genes can still orchestrate the production of necessary growth factors. VEGF genes are used by the body to promote blood-vessel growth. VEGF genes are assimilated (taken in) by muscle cells. The genes cause the muscle cells to make a VEGF protein which promotes the growth of new arteries. VEGF proteins can be made in a lab and injected into a patient intravenously, intraluminally, or intramuscularly to promote the growth of an artery. Or, the genes (or other genetic material) can be applied with an angioplasty balloon, with the assistance of a vector, or by any other method.

It is not always desirable to grow a completely new organ. Sometimes growing a portion of an organ is desirable. For example, in some heart attacks or strokes, a portion of the heart or brain remains viable and a portion dies. An injection of a gene to form cardiac muscle and/or an injection of a gene to form an artery can be utilized to revive or replace the dead portion of the heart. The dead portion of the heart may (or may not) be used as a matrix while the new muscles and vessels grow. Thus, in this example, a partial new organ and is grown in a pre-existing organ. A pacemaker may (or may not) be necessary. A second injection of a gene may (or may not) be necessary to stop cardiac muscle growth once it is completed. Portions of organs throughout the body can similarly be repaired or replaced. It may be necessary to provide gene(s) or growth factor(s) sequentially. For instance, one or more blood vessels are grown by inserting an appropriate gene or other genetic material into a selected area. Second, an appropriate gene or other genetic material is inserted in the selected area to grow a bone or other organ.

The size and shape limitation of the desired structure can come from a containment and boundary contact inhibition phenomenon or by a chemical inhibition.

A variation on the theme of growing a portion of an organ is as follows: a portion of a heart dies. The pericardium is utilized as a scaffold and seeded with cells and/or genes to grow new muscle, and genes (or other genetic material) to grow new arteries. Immediately adjacent the dead cardiac muscle, onto or into the pericardium, the appropriate cells, genes, and/or growth factors (or other genetic material) are placed. Once the new muscle and blood vessels have grown, the function specific tissue can be applied to the damaged portion of the heart and paced, if necessary, to augment cardiac action. If the surgeon desires, the dead muscle can be removed and the new muscle and blood vessels can be surgically rotated into the excised region and secured. This probably can be done endoscopically. In essence, the pericardium is utilized to allow the new muscle wall to grow. The new muscle wall is then transplanted into the damaged heart wall. This procedure utilizes the body as a factory to grow an organ and/or tissue, after which the organ and/or tissue is transplanted to a desired region. On the other hand, the new muscle wall may integrate itself into the old wall and not require transplantation.

It may be advantageous to grow an organ and adjacent tissue. For example, a severe burn victim may lose organs and tissues (skin, blood vessels, fat, muscles, etc.). The gene(s), gene product(s), and/or ECM (or other genetic material) may be assembled utilizing any appropriate delivery vehicle or system. By way of example, and not limitation, four spray cans or other delivery apparatus can be utilized. First, muscle gene in a spray can is applied in a light mist or layer. Then fat, blood vessel, and finally skin gene(s) are applied, each from a separate spray can. Or, possibly, all four components can be admixed in and applied from a single spray can. Carriers, matrixes, isolating layers, and/or form or shape defining products may or may not be used by the operator. All the genes can be in the same spray can or combined with other substances. As can be appreciated by those skilled in the art, any method of inserting the gene(s), grow factors, or ECM into or onto the body can be utilized. Nutrients, analgesics, antiseptics, moisture restoring compositions and methods, and appropriate post-operative dressings can be utilized pursuant to operator discretion on an as-need basis.

It may be desirable to restore a single function in a multifunctional organ. For example, a pancreas produces digestive enzymes and it produces insulin in the Islets of Langerhans. A practitioner may choose to stimulate only a desired portion. For example, inserting a gene for the creation of more Islets of Langerhans can be utilized to selectively restore an appropriate insulin production level without affecting the production of pancreatic digestive enzymes.

There is a mechanotransduction interplay the occurs from the extracellular matrix (ECM) to and across the cell membrane, through the cell's cytoskeleton, and, to the cell's DNA. Cellular products are produced during this process and the process of morphogenesis is aided by this procedure. It may be possible to rejuvenate an organ by inserting a growth factor (especially a growth factor that can mimic extracellular fluid to control cell growth, division, migration, structure, function, and self-assembly) into or around an organ that no longer operates to optimal capacity or to a desired capacity. For example, in the interplay from the ECM to the DNA as described above, if for any reason the DNA falls into disrepair, cellular fitness and function become altered and a disease state may occur. The organ or tissue no longer functions as well as desired. The insertion of the growth factor into or around the organ may rejuvenate and restore the fitness and function to this organ even though the cellular DNA remains is disrepair. This procedure may, in some cases, allow the cell to repair, restore, change and reverse its DNA damage so that it can replicate normally henceforth. Booster shots of the growth factor may be necessary.

Organs and/or tissues can be formed utilizing the patient's own cells. For example, a skin cell(s) is removed from the intraoral lining of a cheek. The cell is genetically screened to identify DNA damage or other structural and/or functional problems. Any existing prior art genetic screening technique can be utilized. Such methods can utilize lasers, DNA probes, PCR, or any other suitable device. If the cell is damaged, a healthy undamaged cell is, if possible, identified and selected. If a healthy cell can not be obtained, the damaged cell can be repaired by excision, alkylation, transition or any other desired method. A growth factor(s) is added to the cell to facilitate dedifferentiation and then redifferentiation and morphogenesis into an organ or function specific tissue. An y machine known in the art can be used to check the genetic fitness of the organ and its stage of morphogenesis. A cell nutrient culture may or may not be utilized depending on the desired functional outcome (i.e., growth of an artery, of pancreatic Islet cells, of a heart, etc.) or other circumstances. Replantation can occur at any appropriate stage of morphogenesis. The foregoing can be repeated without the patient's own cells if universal donor cells such a germinal cells are utilized. Germinal cells do not require a dedifferentiation. They simply differentiate into desired tissues or organs when properly stimulated. Similarly, the DNA utilized in the foregoing procedure can come from the patient or from any desired source.

During reimplantation one of the patient's own cells is returned to the patient. During implantation, a cell not originally obtained from the patient is inserted on or in the patient.

In the example above, if germinal cells (and in some cases, stem cells) are utilized a direct differentiation and morphogenesis into an organ can occur in vivo, ex vivo, or in vitro.

A variant on the above two examples involves inserting a selected gene(s) or portion of a gene into a cell. For example, a cell is removed, analyzed, and repaired if desired or necessary to assure quality (e.g., proper interaction to give structural (protein) or chemical (enzyme) product) and functional outcome (e.g., the production of an organ). A gene(s) or a portion of a gene is secured from the patient cell by sampling or is secured from any other source. The gene is inserted into the cell. A growth factor(s) can be inserted in the cell simultaneously with the gene or at the time preceding or following insertion of the gene. Organ formation occurs and replantation is performed utilizing any acceptable technique. Inserting an appropriate growth factor or other gene product in a cell may, without requiring the insertion of a gene in the cell, trigger the process which causes the cell to grow an organ. Similarly, controlling the ECM contacting a cell can cause mRNA to select and copy a segment of the cell's DNA. This segment of the cell's DNA interacts with one or more components in the cell to produce a growth factor or other gene product which triggers the growth of an organ.

An organ or tissue can be made utilizing pellet, capsule, or other carrier carrying a growth factor, a gene, a growth factor and a gene, or any other desired genetic material. These pellets can include ECM producing compositions or components and can be inserted anywhere in the body. Once inserted in the body, the carriers can be fixed or can be movable; and, they can contain living material, nonliving material, or living and nonliving material. As such, they can be prepackaged pharmaceutical carriers inserted to grow selected tissues and organs. The materials inside the carriers can be from the patient or from any other source. Each carrier can be porous, resorbable, semisolid, gelatinous, or have any other desired physical attribute.

An auxiliary organ or a portion of an auxiliary organ can be grown. For example, a two chambered auxiliary pump for the heart can be grown. Most heart problems occur on the left side. Augmentation and enlargement of the existing heart can help restore optimal function and help prevent pathological enlargement of a poorly performing section of the heart.

An auxiliary organ can be grown in the body years before the anticipated expiration of the original organ. Genetic or other testing can predict organ failure years in advance allowing an early diagnosis of the future failure of an organ.

Avascular necrosis can be corrected with the insertion of a gene(s) and/or growth factor or other genetic material in the body. For example, avascular necrosis is diagnosed near a joint space. VEGF or BMP genes, or, VEGF or BMP growth factors produced by VEFG or BMP genes, respectively, or any other desired genetic based material can be inserted to regrow blood vessels and/or bone. Auxiliary placement apparatus like fixation plates and/or screws, fixing compositions, or any other desired system can be utilized to strengthen or secure tissue. The genes and/or growth factors can, be placed adjacent the auxiliary placement apparatus, can be placed in a composition adjacent the auxiliary placement apparatus, can be placed remote from the auxiliary placement apparatus, or, can be placed at any other desired location.

Cellular dedifferentiation, differentiation, redifferentiation, and morphogenesis are directed and controlled by growth factors (or their genetic counterparts) controlling cell growth, migration, structure, function, and/or self-assembly. A growth factor (or gene or other genetic material) can be inserted into or onto the body to grow missing limbs or body parts. The insertion of a multifactorial and nonspecific growth factor (or gene) is required. Such a growth factor is pluripotent, senses what body part or other component is missing, and directs adjacent cells to reconstruct the body part along genetically predetermined pathways. The process is not unlike the salamander regrowing a severed tail or limb. Other growth factors may or may not be required.

The insertion of a growth factor (or its gene counterpart) in the body can be utilized to prevent and/or reduce inflammation. Growth factors control cell migration. As such, they can be powerful cell inhibitors to prevent inflammatory cells from migrating into an area. Such an application has major usefulness in the treatment of arthritis or other autoimmune or inflammatory diseases. Thus a growth factor can be inserted in the body to control cell migration or to perform other functions described herein.

A rotator cuff deficiency often prevents normal sports activities. Ligament dysfunction can prevent jogging. Venous insufficiency can hinder prolonged standing or walking. Such musculoskeletal injuries or deficiencies can be corrected by inserting a gene(s) and/or growth factor(s) or other genetic material into the body to create new tissue and/or organs which replaces or augments existing tissue.

A hybrid organ or other structure can be fabricated genetically to include specific tissues which function as needed. For example, a kidney containing Islets of Langerhans cells can be produced. Such a kidney is useful for a patient with diabetes mellitus and renal failure. Other hybrid structures can be grown according to need.

Gene Trace Systems, Inc. of Menlo Park, Calif. has developed fully automated DNA sequencing technology that combines DNA probing, sequencing, and sizing reactions with laser-based "time of flight" mass spectrometry. This technology (1) identifies the sequence of base chemicals in a DNA strand in five seconds, (2) permits genetic screening tests that cost as little as a few dollars, and (3) is used for gene discovery and expression, genotyping, and disease diagnosis and identification.

The Biological Microcavity Laser (TBML) analyzes blood and cell samples in minutes. TBML (1) is a kind of "lab-on-a-chip" which utilizes tiny fingers of laser light to image cells which are placed in a small chamber, (2) permits information concerning each cell in a cell sample of millions to be extracted in a few minutes, (3) is a tool for studying cell structure changes and sequencing DNA, (4) can identify the stages of morphogenesis, and (5) is based on a laser device called a VCSEL (vertically-cavity surface-emitting laser). Cells being analyzed with TBML do not have to be killed and stained, as cells normally do for typical laboratory analysis.

Stem cells associated with the central nervous system differentiate to multiple fates: neurons, astrocytes, and oligodendrocytes. The differentiation of these stem cells is influenced by extracellular signals. For example, platelet-derived growth factor is known to support neuronal differentiation. In contrast, ciliary neurotrophic factor and thyroid hormone T3 act on stem cells to generate astrocytes and oligodendrocytes.

Pax genes are key regulators during organogenesis of kidney, eye, ear, nose, limb muscle, vertebral column and brain.

The extracellular matrix (ECM) is a dense, fibrous network of proteins and sugars forming a complex natural environment surrounding individual cells or groups of cells. Components of the matrix, including proteins such a laminin and fibronectin, bind to specific molecules called integrins on the cell surface. Through these integrins the matrix sends cells various signals that regulate what genes are active. These signals ultimately influence whether cells proliferate, specialize, migrate, or even eliminate themselves. The ECM has the ability to command cells to use particular, tissue-specific genes. This allows the microenvironment outside of cells to confer tissue specificity. For example, capillary epithelial cells roll up to form normal blood vessels only if grown on the proper matrix molecules.

A gene corresponds to a segment of the DNA that codes for the synthesis of a single polypeptide chain. The definition of a gene product, as used herein, is the polypeptide or ribosomal RNA coded for by a gene, i.e., which a gene causes to be produced. A gene product can include proteins, transcription factor(s), and/or RNA. For example, VEGF is a gene, while VEGF growth factor is a gene product.

Genes, a gene, a portion of a gene, ECM, and/or a nutrient media can be inserted into a cell or groups of cells by direct insertion (for example, an apparatus like a micropipette), with a cell fragment (for example, a plasmid from a bacterium), with a virus vector, liposome, by phagocytosis, with the help of pore-forming substance, electrically, chemically, or by any other desired technique of crossing the cell membrane to reach the nucleus or any other desired site in the cell. A gene(s) can be transferred in the form of naked plasmid DNA. For example, an intramuscular injection can be made of plasmid DNA encoding the secreted angiogenic growth factor such as vascular endothelial growth factor (VEGF).

In accordance with one embodiment of the invention, a gene, growth factor, ECM (or other genetic material) and/or nutrient media is inserted into or onto the body at a specific location to induce and promote the morphogenesis and growth of an organ or desired organ sub-structure at that location. A desired organ sub-structure can comprise a cell, group of cells, neuron, dermis, Islet cells, etc. Also in accordance with the invention, a gene or other genetic material is inserted into or onto a cell or group of cells outside the body to induce and promote morphogenesis and growth of an organ or desired structure. Growth factors can also be utilized in combination with or in place of a gene. The resulting induced organ or other structure is transplanted to a desired location in a patient's body.

Gene products can be inserted in a patient's body to produce an organ or other structure. For example, VEGF growth factor inserted in the body produces an organ, i.e., an artery.

Selected ECM compositions or other environmental factors can induce the morphogenesis of organs or selected organ sub-structures. As used herein, environmental factors include, but are not limited to, compositions which exert physical, mechanical, chemical, electrical, and/or structural forces on living cells.

Another variant of the invention inserts a gene and a growth factor at a selected location or locations in the body of a patient to grow a selected organ or structure. As exemplified by cloning technology, an enucleated ovum is a viable growth factor. Other subunits of a cell also qualify as growth factors. A gene and the extracellular matrix may also be inserted at a selected location or locations in a patient's body to grow an organ. Likewise, a growth factor and the extracellular matrix can be inserted in a patient's body to form an organ.

EXAMPLE 18

A 36 year old Caucasian male experiences pain in his left leg. A medical examination reveals a damaged one inch long section of a large artery in his left leg. The examination also reveals that this damaged section of the artery is nearly completely clogged with plaque and that the wall of the artery is weakened. The weakening in the arterial wall makes attempting to clean out the artery risky and also makes it risky to attempt to insert a stent in the artery.

Recombinant cDNA encoded to combine with a cell ribosome to produce the human growth factor VEGF is assembled into a eukaryotic expression plasmid. The recombinant cDNA is from cDNA libraries prepared from HL60 leukemia cells and is known to cause the growth of arteries. The plasmid is maintained at a room temperature of 76 degrees F.

The clones are placed in 1.0 milliliters of a normal saline carrier solution at a room temperature of 76 degrees F. to produce an genetic carrier solution. The genetic carrier solution contains about 250 ug of the cDNA clones. A nutrient culture can, if desired, be utilized in conjunction with or in place of the saline carrier. Each clone is identical. If desired, only a single clone can be inserted in the normal saline carrier solution. The saline carrier solution comprises 0.09% by weight sodium chloride in water. A saline carrier solution is selected because it will not harm the DNA clone.

Two sites are selected for injection of the genetic carrier solution. While the selection of sites can vary as desired, the sites are selected at the lower end (the end nearest the left foot of the patient) of the damaged section of the artery so that the new arterial section grown can, if necessary, be used to take the place of the damaged section of the artery in the event the damaged section is removed.

The first site is on the exterior wall of the artery on one side of the lower end of the damaged section of the artery. A containment system is placed at the first site.

The second site is inside the wall of the artery on the other side of the lower end of the artery.

The genetic carrier solution is heated to a temperature of 98.6 degrees F. 0.25 milliliters of the genetic carrier solution is injected into the containment system at the first site. 0.25 milliliters of the genetic carrier solution is injected at the second site inside the wall of the artery. Care is taken to slowly inject the genetic carrier solution to avoid entry of the solution into the artery such that blood stream will carry away the cDNA in the solution.

After two weeks, an MRI is taken which shows the patient's leg artery. The MRI reveals new growth at the first and second sites.

After four weeks, another MRI is taken which shows the patient's leg artery. The MRI shows that (1) at the first site a new artery is growing adjacent the patient's original leg artery, and (2) at the second site a new section of artery is growing integral with the original artery, i.e., at the second site the new section of artery is lengthening the original artery, much like inserting a new section of hose in a garden hose concentric with the longitudinal axis of the garden hose lengthens the garden hose.

After about eight to twelve weeks, another MRI is taken which shows that the new artery growing adjacent the patient's original artery has grown to a length of about one inch and has integrated itself at each of its ends with the original artery such that blood flows through the new section of artery. The MRI also shows that the new artery at the second site has grown to a length of one-half inch.

In any of the examples of the practice of the invention included herein, cell nutrient culture can be included with the gene, the growth factor, the extracellular matrix, or the environmental factors.

In any of the examples of the practice of the invention included herein, the concept of gene redundancy can be applied. For example, the Examples 1 to 14 concerning a tooth list the genes MSX-1 and MSX-2. These genes differ by only two base pairs. Either gene alone may be sufficient. A further example of redundancy occurs in growth factors. Looking at the Examples 10 to 14, BMP4 or BMP2 alone may be sufficient. Redundancy can also be utilized in connection with transcription factors, extracellular matrices, environmental factors, cell nutrient cultures, physiological nutrient cultures, vectors, promoters, etc.

One embodiment of the invention inserts genetic material (gene, growth factor, ECM, etc.) into the body to induce the formation of an organ. Similar inducing materials inserted ex vivo into or onto a living cell in an appropriate physiological nurturing environment will also induce the growth of an organ. The VCSEL laser allows early detection in a living cell of a morphogenic change indicating that organ formation has been initiated. With properly timed transplantation, organ growth completes itself.

During the ex vivo application of the invention, a gene and/or growth factor is inserted into a cell or a group of cells; an ECM or environmental factor(s) are placed around and in contact with a cell or group of cells; or, genetic material is inserted into a subunit of a cell to induce organ growth. An example of a subunit of a cell is an enucleated cell or a comparable artificially produced environment. In in vivo or ex vivo embodiments of the invention to induce the growth of an organ, the genes, growth factors, or other genetic material, as well as the environmental factors or cells utilized, can come from any desired source.

EXAMPLE 19

Genetically produced materials are inserted in the body to cause the body to grow, reproduce, and replace in vivo a clogged artery in the heart. This is an example of site-specific gene expression. A plasmid expression vector containing an enhancer/promoter is utilized to aid in the transfer of the gene into muscle cells. The enhancer is utilized to drive the specific expression of the transcriptional activator. After the enhancer drives the expression of the transcriptional activator, the transcriptional activator transactivates the muscle/artery genes. Saline is used as a carrier. Cardiac muscle can take up naked DNA injected intramuscularly. Injecting plasmid DNA into cardiac (or skeletal) muscle results in expression of the transgene in cardiac myocytes for several weeks or longer.

Readily available off-the-shelf (RAOTS) cDNA clones for recombinant human VEGF165, isolated from cDNA libraries prepared from HL60 leukemia cells, are assembled in a RAOTS expression plasmid utilizing 736 bp CMV promoter/enhancer to drive VEGF expression. Other RAOTS promoters can be utilized to drive VEGF expression for longer periods of time. Other RAOTS recombinant clones of angiogenic growth factors other than VEGF can be utilized, for example, fibroblast growth factor family, endothelial cell growth factor, etc. Downstream from the VEGF cDNA is an SV40 polyadenylation sequence. These fragments occur in the RAOTS pUC118 vector, which includes an *Escherichia coli* origin of replication and the Beta lactamase gene for ampicillin resistance.

The RAOTS construct is placed into a RAOTS 3 ml syringe with neutral pH physiologic saline at room temperature (or body temperature of about 37 degrees C.). The syringe has a RAOTS 27 gauge needle.

Access to the cardiac muscle is gained by open heart surgery, endoscopic surgery, direct injection of the needle without incision, or by any other desired means. The cardiac muscle immediately adjacent a clogged artery is slowly injected with the RAOTS construct during a five second time period. Injection is slow to avoid leakage through the external covering of muscle cells. About 0.5 ml to 1.0 ml (milliliter) of fluid is injected containing approximately 500 ug phVEGF165 in saline (N=18). The readily available off-the-shelf cDNA clones cause vascular growth which automatically integrates itself with the cardiac muscle. Anatomic evidence of collateral artery formation is observed by the 30th day following injection to the RAOTS construct. One end of the artery integrates itself in the heart wall to receive blood from the heart. The other end of the artery branches into increasing smaller blood vessels to distribute blood into the heart muscle. Once the growth of the new artery is completed, the new artery is left in place in the heart wall. Transplantation of the new artery is not required.

Blood flow through the new artery is calculated in a number of ways. For example, Doppler-derived flow can be determined by electromagnetic flowmeters (using, for example, a Doppler Flowmeter sold by Parks Medical Electronic of Aloha, Oreg.) both in vitro and in vivo. RAOTS external ultrasound gives a semiquantitative analysis of arterial flow. Also, RAOTS angiograms or any other readily available commercial devices can be utilized.

VEGF gene expression can be evaluated by readily available off-the-shelf polymerase chain reaction (PCR) techniques.

If controls are desired, the plasmid pGSVLacZ containing a nuclear targeted Beta-galactosidase sequence coupled to the simian virus 40 early promoter can be used. To evaluate efficiency, a promoter-matched reporter plasmid, PCMV Beta (available from Clontech of Palo Alto, Calif.), which encodes Beta-galactosidase under control of CMV promoter/enhancer can be utilized. Other RAOTS products can be utilized if desired.

EXAMPLE 20

A patient, a forty year old African-American female in good health, has been missing tooth number 24 for ten years. The space in her mouth in which her number 24 tooth originally resided is empty. All other teeth except tooth number 24 are present in the patient's mouth. The patient desires a new tooth in the empty "number 24" space in her mouth.

A full thickness mucoperiosteal flap surgery is utilized to expose the bone in the number 24 space. A slight tissue reflection into the number 23 tooth and number 25 tooth areas is carried out to insure adequate working conditions.

A Midwest Quietair handpiece (or other off-the-shelf handpiece) utilizing a #701 XXL bur (Dentsply Midwest of Des Plaines, Ill.) (a #700, #557, #558, etc. bur can be utilized if desired) is used to excavate an implant opening or site in the bone. The implant opening is placed midway between the roots of the number 23 and number 25 teeth. The opening ends at a depth which is about fifteen millimeters and which approximates the depth of the apices of the roots of the number 23 and number 25 teeth. Care is taken not to perforate either the buccal or lingual wall of the bone. In addition, care is taken not to perforate or invade the periodontal ligament space of teeth numbers, 23 and 25.

An interrupted drilling technique is utilized to avoid overheating the bone when the #701XXL bur is utilized to form the implant opening. During a drilling sequence, the drill is operated in five second increments and the handpiece is permitted to stall. Light pressure and a gentle downward stroke are utilized. The bur is removed from the opening after the handpiece is permitted to stall. This sequence is repeated until an implant opening having the desired depth is created. In the event a standard off-the-shelf implant drill is utilized, the foregoing technique is not utilized and, instead, the manufacturer's recommended drilling technique is followed.

Once the implant opening is created, 0.5 ml of EDTA (ethylene diamine tetra acetic acid) is lavaged to the bottom of the implant opening or site and allowed to set for two minutes. The EDTA solution is then washed off with sterile water. This removes the smear layer which forms when the #701XXL bur is used to form the implant opening.

0.5 cc of propylene glycol alginate solution is mixed with freeze dried MSX-1 matrix proteins. The resultant gel is backloaded into a Luhrlock syringe through an 18 gauge needle. Once loaded, a smaller 27 gauge needle is be placed on the syringe to allow the need to be bent when it is inserted in the implant site in the mouth. The gel loses handling qualities after about two hours and is therefore preferably utilized within ten or fifteen minutes after being admixed.

The tip of the 27 gauge needle is placed at the bottom of the implant opening and 0.25 ml of gel is ejected into the bottom of the implant opening. The needle is slowly removed from the implant opening while, at the same time, the syringe is operated to express additional gel to fill the implant opening from the bottom of the opening to the coronal aspect of the bone surrounding the implant opening. Gum tissue is drawn over the implant opening to close the opening and is sutured in place with Ethicon suture.

Alginate gel begins to be absorbed by the patient's body within 48 hours and binds MSX-1 proteins to bone in or adjacent the implant opening. Within about six (6) months, the formation of a tooth is radiographically confirmed.

EXAMPLE 21

Example 20 is repeated, except that the MSX-1 alginate matrix proteins are omitted, and in their place at least one MSX-1 gene, a plasmid, and a promoter/enhancer are mixed with and included in the gel that is loaded into the syringe and injected into the implant opening. Similar results are obtained.

EXAMPLE 22

Example 21 is repeated, except a 0.09% saline solution is utilized as a carrier instead of the alginate gel. Similar results are obtained.

EXAMPLE 23

Example 21 is repeated, except a MSX-2 gene is utilized in place of the MSX-1 gene. Similar results are obtained.

EXAMPLE 24

Example 22 is repeated, except a MSX-2 gene is utilized in place of the MSX-1 gene. Similar results are obtained.

EXAMPLE 25

Example 21 is repeated, except a PAX-9 gene is utilized in place of the MSX-1 gene. Similar results are obtained.

EXAMPLE 26

Example 22 is repeated, except a PAX-9 gene is utilized in place of the MSX-1 gene. Similar results are obtained.

EXAMPLE 27

Example 21 is repeated, except a PAX-9 protein is utilized in place of the MSX-1 gene. Similar results are obtained.

EXAMPLE 28

Example 22 is repeated, except a PAX-9 protein is utilized in place of the MSX-1 gene. Similar results are obtained.

EXAMPLE 29

Example 21 is repeated, except at least one MSX-2 gene is included in combination with the MSX-1 gene. Similar results are obtained.

EXAMPLE 30

Example 22 is repeated, except at least one MSX-2 gene is included in combination with the MSX-1 gene. Similar results are obtained.

EXAMPLE 31

Example 21 is repeated, except at least one MSX-2 gene is included in combination with the MSX-1 gene along with BMP2, BMP4, and BMP7 growth factors. Similar results are obtained.

EXAMPLE 32

Example 22 is repeated, except at least one MSX-2 gene is included in combination with the MSX-1 gene along with BMP2, BMP4, and BMP7 growth factors. Similar results are obtained.

For the development of a tooth in accordance with the invention, an upstream initiator gene(s) and/or growth factor(s) inserted directly in vivo or transplanted into the body at a very early stage of morphogenesis is sufficient for tooth formation. The general approach delineated above for a tooth and an artery is appropriate for any organ or organ system. When an organ is grown ex vivo other regulator and/or signaling compositions can be utilized in addition to initiator genes (like MSX-1) and/or growth factors. During growth of a tooth, the genetically produced materials noted below can be utilized:

| Initiation | Proliferation | Morphogenesis |
|---|---|---|
| Bmp2,4 | Bmp2,4 | Bmp4 |
| EGF | Dlx1-3 | Collagens |
| FGF8 | EGR1 | Dlx1-3 |
| Lef1 | FGFs | Lef1 |
| Msx1 | Lef1 | Msx1 |
| Msx2 | Msx1 | Msx2 |
| Shh | Msx2 | Notch1-3 |
|  | Notch1-3 | Pax9 |
|  | Pax9 | RAR |
|  | RAR (alpha, beta omega) | RXR |
|  | RXR (alpha, beta omega) | Tuftelin |
|  | Syndecan |  |
|  | Tenascin |  |
|  | TGF-beta s |  |

In the Islets of Langerhans, the initiators are: Pax-6, Pax4, ISL-1, NKX6A. Other factors are the TGF family, Gastrin, IDX-1, PDX-1, INGAP, NeuroD, HNF3beta, IPF-1, helix-loop-helix protein Beta-2, etc.

In accordance with the invention, site preparation prior to the insertion of a gene and/or growth factor into the body can occur at any selected site. For example, examples of site preparation include debridement of a burn wound, the application of EDTA or citric acid to a bone site, or any other desired site preparation.

As used herein, genetic material includes a gene(s), a portion of a gene, a growth factor(s), a gene product(s), and/or ECM which individually or collectively function to cause the genesis and growth of an organ.

EXAMPLE 33

Example 18 is repeated except that the patient is a 24 year old Caucasian male and the genetic carrier solution is injected into two sites in the right leg of the patient. The first site is on the exterior wall on one side of the right leg artery. The second site is inside the wall of the right leg artery on the other side of the artery. The right leg artery is not blocked and is a normal healthy artery. Similar results are obtained, i.e., a new section of artery grows integral with the original right leg artery, and a new section of artery grows adjacent the original right leg artery.

EXAMPLE 34

Example 18 is repeated except that VEGF growth factor is utilized in the genetic carrier solution in place of the cDNA. Similar results are obtained.

EXAMPLE 35

Example 18 is repeated except that the patient is a 32 year old Caucasian female, the cDNA produces a VEGF growth factor which promotes the growth of veins, and the genetic carrier solution is injected into two sites in the right leg of the patient. The first site is on the exterior wall on one side of a large right leg vein. The second site is inside the wall of the right leg vein on the other side of the vein. The right leg vein is not blocked and is a normal healthy artery. Similar results are obtained, i.e., a new section of vein grows integral with the original right leg vein, and a new section of vein grows adjacent the original right leg vein.

EXAMPLE 36

Example 18 is repeated except that the patient is a 55 year old Caucasian male, and the genetic carrier solution is injected into two sites in the coronary artery of the patient. The first site is on the exterior wall on one side of the artery. The second site is inside the wall of the artery on the other side of the artery. A section of the artery is damaged, is partially blocked, and has a weakened wall. The first and second sites are each below the damaged section of the artery. Similar results are obtained, i.e., a new section of artery grows integral with the original artery, and a new section of artery grows adjacent the original artery. The new section of artery has integrated itself at either end with the original artery so that blood flows through the new section of artery.

Having described my invention in such terms as to enable those skilled in the art to understand and practice it, and having described the presently preferred embodiments thereof, I claim:

1. A method of growing and integrating a desired artery at a selected site in a body of a human patient comprising the steps of locally placing living stem cells harvested from bone marrow in a body of a human patient at said selected site and growing said desired artery which integrates itself into said body at said selected site.

* * * * *